(12) United States Patent
Bowman et al.

(10) Patent No.: US 9,879,012 B2
(45) Date of Patent: *Jan. 30, 2018

(54) CLICK NUCLEIC ACIDS

(71) Applicant: THE REGENTS OF THE UNIVERSITY OF COLORADO, A BODY CORPORATE, Denver, CO (US)

(72) Inventors: Christopher N. Bowman, Boulder, CO (US); Christopher J. Kloxin, Newark (DE); Weixian Xi, Boulder, CO (US)

(73) Assignee: REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 418 days.

This patent is subject to a terminal disclaimer.

(21) Appl. No.: 14/388,748

(22) PCT Filed: Mar. 12, 2013

(86) PCT No.: PCT/US2013/030538
§ 371 (c)(1),
(2) Date: Sep. 26, 2014

(87) PCT Pub. No.: WO2013/148165
PCT Pub. Date: Oct. 3, 2013

(65) Prior Publication Data
US 2015/0057187 A1    Feb. 26, 2015

Related U.S. Application Data

(60) Provisional application No. 61/617,145, filed on Mar. 29, 2012.

(51) Int. Cl.
*C07D 473/34* (2006.01)
*C07D 473/18* (2006.01)
(Continued)

(52) U.S. Cl.
CPC ......... *C07D 473/34* (2013.01); *C07D 239/47* (2013.01); *C07D 239/54* (2013.01);
(Continued)

(58) Field of Classification Search
CPC .. C07D 473/34; C07D 473/18; C07D 239/54; C07D 239/47; C12Q 1/6876
(Continued)

(56) References Cited

U.S. PATENT DOCUMENTS 6,075,143 A    6/2000 Breipohl et al.
2009/0124534 A1    5/2009 Reineke
(Continued)

FOREIGN PATENT DOCUMENTS

CA    2078256 A1    3/1994
JP    258222 A    10/1995
(Continued)

OTHER PUBLICATIONS

International Search Report and Written Opinion dated May 20, 2013 for PCT/US2013/030538, pp. 1-12.
(Continued)

*Primary Examiner* — Jezia Riley
(74) *Attorney, Agent, or Firm* — Richard S. Echler; Jason K. Pass; FisherBroyles, LLP

(57) ABSTRACT

Click nucleic acid monomers and polymers containing such monomers are disclosed. The click nucleic acid monomers include an optionally protected thiol moiety, an optionally protected thiol-click acceptor moiety, and an optionally protected nucleobase (NB), which in some examples is an A, G, T, U, or C nucleobase. In some examples, the click nucleic acid monomer includes a N-vinyl thiol acetamide (VTA) backbone. In other examples the click nucleic acid monomer includes a N-vinyl thiol ethylamine (VTE) backbone. Methods of using such polymers, for example in place (Continued)

of naturally occurring nucleic acid polymer applications, such as DNA or RNA, and synthetic nucleic acid polymer applications, such as PNA or morpholino nucleic acids, are also disclosed.

11 Claims, 13 Drawing Sheets

(51) Int. Cl.
  *C07D 239/47* (2006.01)
  *C07D 239/54* (2006.01)
  *C12Q 1/68* (2006.01)

(52) U.S. Cl.
  CPC ......... *C07D 473/18* (2013.01); *C12Q 1/6876* (2013.01); *C12Q 2600/156* (2013.01)

(58) Field of Classification Search
  USPC ........................................................ 536/4.1
  See application file for complete search history.

(56) References Cited

U.S. PATENT DOCUMENTS

| | | | |
|---|---|---|---|
| 2011/0077407 A1 | 3/2011 | David et al. | |
| 2011/0129921 A1 | 6/2011 | Johnson et al. | |
| 2011/0171448 A1 | 7/2011 | Tang et al. | |
| 2012/0071641 A1 | 3/2012 | Manoharan et al. | |

FOREIGN PATENT DOCUMENTS

| | | |
|---|---|---|
| WO | 1989012060 A1 | 12/1989 |
| WO | 1995031470 A2 | 11/1995 |
| WO | 199604295 A1 | 2/1996 |
| WO | 2010048549 A2 | 4/2010 |

OTHER PUBLICATIONS

Mourtas et al., "S-4 Methoxytrityl Mercapto Acids: Synthesis and Application," Tetrahedron Letters, vol. 42, Issue 39, Sep. 24, 2001, pp. 6965-6967.

PubChem Record CID 2245987, URL: http://pubchem.ncbi.nlm.nih.gov/summary/summary.cgi?cid=2245987, Create Date: Jul. 15, 2005, Accessed: Apr. 13, 2013, pp. 1-3.
PubChem Record CID 201366, URL: http://pubchem.ncbi.nlm.nih.gov/summary/summary.cgi?cid=201366, Create Date: Aug. 9, 2005, Accessed: Apr. 13, 2013, pp. 1-3.
PubChem Record CID 5232652, URL: http://pubchem.ncbi.nlm.nih.gov/summary/summary.cgi?cid=5232652, Create Date: Oct. 7, 2005, Accessed: Apr. 13, 2013, pp. 1-3.
Chinese Office Action issued in CN Patent Application No. 201380024075.7 dated Feb. 14, 2017, with English translation of same (13 pages).
English Translation of Second Office Action dated Jun. 20, 2016, in Chinese Patent Application No. CN 201380024075.7 (9 pages).
Communication Pursuant to Rules 70(2) and 70a(2) EPC dated Jun. 17, 2016 in European Patent Application No. 13767244.0 (1 page).
Extended European Search Report dated May 31, 2016 in European Patent Application No. 13767244.0 (9 pages).
Dose et al., "Convergent synthesis of peptide nucleic acids by native chemical ligation", Org Lett. Sep. 29, 2005;7 (20):4365-8.
Gogoi et al., "Sugar-thioacetamide backbone in oligodeoxyribonucleosides for specific recognition of nucleic acids", Chem Commun (Camb). Jun. 14, 2006;(22):2373-5. Epub Apr. 25, 2006.
Pensato et al., "New Synthetic Rout to [gamma]-Mercaptomethyl PNA Monomers", Synthetic Communications, vol. 38, No. 15, Jul. 24, 2008 (2008) , pp. 2499-2506, XP055272645, Philadelphia, PA; US ISSN: 0039-7911t DOI: 10.1088/00397910802219122.
Scheibe et al., "DNA-programmed spatial screening of carbohydrate-lectin interactions", Chemical Science, vol. 2, No. 4, Jan. 1, 2011 (Jan. 1, 2011) pp. 770, XP055272631, United Kingdom, ISSN: 2041-6520, DOI: 10.1039/c0c00565g.
Konkolewicz et al., "Hyperbranched polymers by thiol-yne chemistry: from small molecules to functional polymers", J Am Chem Soc. Dec. 23, 2009;131(50):18075-7. doi: 10.1021/ja908206a.
English Translation of First Office Action issued Sep. 6, 2015, in Chinese Patent Application No. CN 201380024075.7 (8 pages).
Japanese Office Action issued in JP Patent Application No. 2015-503259 dated Oct. 18, 2016, with English translation of same (16 pages).
Hoyle et al., "Thiol-click chemistry: a multifaceted toolbox for small molecule and polymer synthesis", Chem Soc Rev. Apr. 2010;39(4):1355-8T doi: 10.1039/b901979k. Epub Feb. 9, 2010.
Zhang et al., "Synthesis and hybridization property of an oligonucleotide containing a 3-thioformacetal linked pentathymidylate", Bioorg Med Chem Lett. Feb. 8, 1999;9(3):319-22.

CLICK NUCLEIC ACIDS

CROSS-REFERENCE TO RELATED APPLICATION

This application is the U.S. National Stage of International Application No. PCT/US2013/030538, filed Mar. 12, 2013, published in English under PCT Article 21(2), which claims the priority benefit of U.S. Provisional Application No. 61/617,145, filed on Mar. 29, 2012, which is incorporated herein by reference in it entirety.

This invention was made with government support under grant number R21CA174479 awarded by the National Institutes of Health. The government has certain rights in the invention.

FIELD

This disclosure relates to nucleic acid mimetics, and specifically to nucleic acid mimetics having a thioether backbone, methods of producing such nucleic acid mimetics and use thereof.

BACKGROUND

Nucleic acid-based molecules, such as DNA, RNA, and PNA, have continued to find ever-increasing levels of implementation and exciting applications in biology and biomedical systems, whether for gene knockout, as aptamers, for drug delivery and targeting, in biodetection, and in many other areas.

DNA is one of the most capable and powerful molecules: functional as genetic material or as aptamers, hybridizing to complementary strands, active in transcription/translation and able to induce organization and formation of nanostructures. Unfortunately, technical utilization of DNA remains prohibitively expensive and/or difficult to implement in any but the most valuable applications, particularly as materials. As a synthetic alternative, peptide nucleic acids (PNAs) were developed and found to hybridize with complimentary PNA or DNA molecules.

The first PNA was synthesized using an aminoethylglycine (AEG) backbone, which was selected based on rudimentary molecular modeling that indicated similar repeat-unit distances and optimized bond angles to that of the phosphate-ribose backbone of DNA. Since its discovery, several variations of PNAs have been synthesized and evaluated, revealing basic structural constraints required for hybridization. The most critical constraint appears to be the distance between pendant nucleobases along the backbone of the chain—the optimum of which is six atoms. While hybridization with ssDNA has been observed for PNAs possessing a 5- or 7-atom spacer between nucleobases, PNA backbone variations having a 6-atom spacer exhibit greater stability as indicated by their higher melting temperatures. PNAs have been used extensively in self-assembly and targeted drug delivery. Despite PNA's advantages over DNA, they are limited by the characteristics of the formation reactions as well as the peptidic backbone. Among those problems are the need for large reactant excesses, relatively slow reaction kinetics, and numerous concerns over side reactions. Thus, there is a need for additional nucleic acid mimetics. The current disclosure meets this need.

SUMMARY

Disclosed herein are monomeric CNA molecule, structures or building blocks that can be used to create poly thio-ether nucleic acid. In some embodiments a thio-ether nucleic acid monomer, includes an optionally protected thiol moiety, an optionally protected thiol-click acceptor, an optionally protected nucleobase and a backbone that includes an atom with a valency of 3 or more, such as carbon (C), nitrogen (N), or boron (B). The thiol, the thiol-click acceptor, and the nucleobase are independently linked to the backbone through covalent linkages. In some examples, the backbone includes additional atoms with a valency of 3 or more. In some embodiments, the thio-ether nucleic acid monomer further includes a linker, wherein the linker covalently links the nucleobase to the atom with the valency of 3 or more. In some examples, the linker includes —C(O)C—. In some embodiments, the linker and the nucleobase are a nucleobase sidechain (NS).

In some embodiments, a click nucleic acid monomer has the following structure:

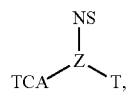

where is Z is a backbone atom having a valency of 3 or more, such as C, N, or B boron, NS is a nucleobase side-group, which includes an optionally protected nucleobase (NB) and optionally a linker, linking the NB and Z, T is an optionally protected thiol, and TCA is an optionally protected thiol-click acceptor.

In some embodiments, a click nucleic acid backbone includes one or more additional atoms with a valency of 3 or more, such as C, N, or B.

In some embodiments, a click nucleic acid monomer has the structure:

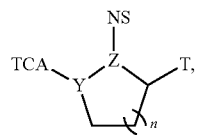

where Y and Z are atoms having a valency of 3 or more (for example carbon, nitrogen, and boron), n is an integer of from 0 to 4, NS is a nucleobase side-group, which includes an optionally protected nucleobase, T is an optionally protected thiol and TCA is an optionally protected thiol-click acceptor.

In some embodiments, a click nucleic acid monomer has the structure:

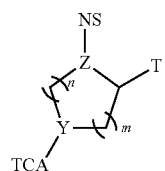

where Y and Z are atoms having a valency of 3 or more, n and m are independently integers of from 0 to 4, NS is a nucleobase side-group, which includes an optionally protected nucleobase, T is an optionally protected thiol and TCA is an optionally protected thiol-click acceptor.

In some embodiments, a click nucleic acid monomer has the structure:

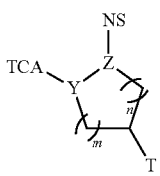

where Y and Z are atoms having a valency of 3 or more, n and m are independently integers of from 0 to 4, NS is a nucleobase side-group, which includes an optionally protected nucleobase, T is an optionally protected thiol and TCA is an optionally protected thiol-click acceptor.

In some embodiments, click acid monomer has the following structure:

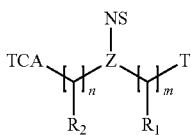

where, n+m is between 1 and 7, n>0, and m>0, NS is a nucleobase side group, including an optionally protected nucleobase, T is an optionally protected thiol and TCA is optionally protected thiol-click acceptor, Z is an atom with a valency of 3 or more, and $R_1$ and $R_2$ are independently a combination of hydrogen, hydroxyl, aromatic, amine, carboxyl, and carbonyl groups, optionally substituted.

In some embodiments, the click nucleic acid monomer further includes a linker, wherein the linker covalently links the nucleobase to the atom with the valency of 3 or more. In some examples, the linker includes —C(O)C—. In some embodiments, a disclosed click nucleic acid monomer includes a N-vinyl thiol acetamide (VTA) backbone. In other embodiments, a disclosed click nucleic acid monomer includes a N-vinyl thiol ethylamine (VTE) backbone.

Also disclosed are click nucleic acid polymers that include a disclosed thio-ether nucleic acid monomer, such as one or more of the disclosed thio-ether monomers. Such polymers are end linked between the thiol moiety and the terminal end of the thiol-click acceptor moiety. In some examples, the CNA molecules are conjugated to one or more additional molecules, such as effector molecules. In some embodiments, for example as a therapeutic, the thio-ether nucleic acid polymer is provided as a composition, such as a composition that includes a pharmaceutically acceptable carrier. Methods of using such polymers, for example in place of DNA, RNA, morpholino nucleic acids (MNA) and/or synthetic nucleic acid mimetics, such as PNAs, are also contemplated.

The foregoing and other, features, and advantages of this disclosure will become more apparent from the following detailed description, which proceeds with reference to the accompanying figures.

BRIEF DESCRIPTION OF THE DRAWINGS

FIG. 2 is a schematic of an exemplary generalized radical-mediated thiol-ene 'click' reaction mechanism. The thiolene reaction undergoes a rapid sequential propagation and chain transfer mechanism yielding the highly selective addition between a thiol and vinyl ('ene') functional group. The extremely high reaction efficiency enables a low concentration of photoinitiator to achieve spatiotemporal control of the reaction. For CNA polymer formation, $R_1$ is and $R_2$ represent the first and second CNA monomer in a CNA polymerization reaction respectively. While the thiol-ene reaction mechanism is depicted, as disclosed herein the reaction can occur between the thiol moiety and any thiol-click acceptor, such as an alkyne, halide, isocyanate or epoxy moiety and the like.

BRIEF DESCRIPTION OF THE SEQUENCE LISTING

Figure 1:
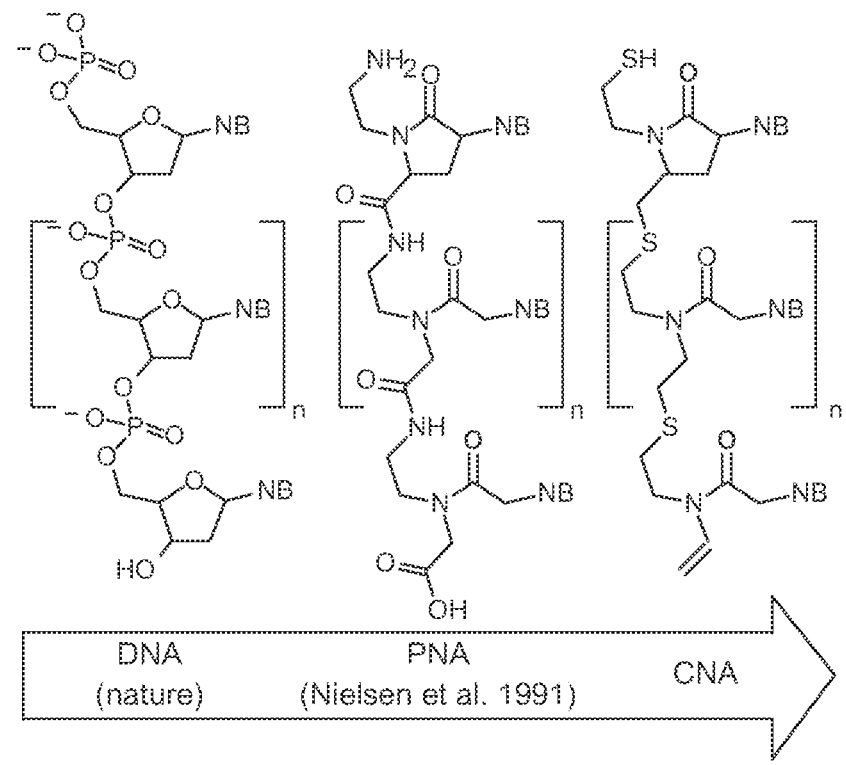
FIG. 1 shows possible structures of the oligonucleotide classes DNA, PNA and CNA. Depicted is the structural evolution of the backbone polymer from the natural biopolymer DNA to artificial biopolymers of PNA and one possible CNA structure, as disclosed herein. In this example, the CNA backbone is designed to have similar molecular spacing to both PNA and DNA, have a thio-ether backbone formed from the thiol-ene click reaction disclosed herein, and have the capacity for hybridization with other oligonucleotides including DNA to induce controlled assembly and biofunctionality.

The nucleic and amino acid sequences shown herein are shown using standard letter abbreviations for nucleotide bases and amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named COL_0110WP_ST25.txt, which was created on Mar. 11, 2013, is 1 kilobyte, and is incorporated by reference herein.

SEQ ID NOs: 1 and 2 are exemplary nucleic acid sequences of KRAS.

DETAILED DESCRIPTION

I. Summary of Terms

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Unless otherwise noted, technical terms are used according to conventional usage. Definitions of common terms in molecular biology may be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710). Definitions of common terms in chemistry may be found in Richard J. Lewis, Sr. (ed.), *Hawley's Condensed Chemical Dictionary*, published by John Wiley & Sons, Inc., 1997 (ISBN 0-471-29205-2).

To facilitate review of the various embodiments of the disclosure, the following explanations of specific terms are provided:

Administration: To provide or give a subject an agent, such as a click nucleic acid (CNA) described herein, by any effective route. Exemplary routes of administration include, but are not limited to, topical, injection (such as subcutaneous, intramuscular, intradermal, intraperitoneal, intratumoral, and intravenous), oral, sublingual, rectal, transdermal, intranasal, vaginal and inhalation routes.

Animal: A living multicellular vertebrate organism, a category that includes, for example, mammals. A "mammal" includes both human and non-human mammals, such as mice. The term "subject" includes both human and animal subjects, such as mice. In some examples, a subject is a patient.

Antisense compound: Refers to an oligomeric compound that is at least partially complementary to the region of a target nucleic acid molecule (for example a CNA having nucleobases that are at least partially complementary) to which it hybridizes. As used herein, an antisense compound that is "specific for" a target nucleic acid molecule is one which specifically hybridizes with and modulates expression of the target nucleic acid molecule. As used herein, a "target" nucleic acid is a nucleic acid molecule to which an antisense compound is designed to specifically hybridize and modulate expression.

Nonlimiting examples of antisense compounds include primers, probes, antisense oligonucleotides, and CNAs comprising the same.

Alkoxy: A —$OZ_1$ radical, where $Z_1$ is selected from the group consisting of alkyl, substituted alkyl, cycloalkyl, substituted cycloalkyl, heterocycloalkyl, substituted heterocycloalkyl, silyl groups and combinations thereof as described herein. Suitable alkoxy radicals include, for example, methoxy, ethoxy, benzyloxy, t-butoxy, and the like. A related term is "aryloxy" where $Z_1$ is selected from the group consisting of aryl, substituted aryl, heteroaryl, substituted heteroaryl, and combinations thereof. Examples of suitable aryloxy radicals include phenoxy, substituted phenoxy, 2-pyridinoxy, 8-quinalinoxy and the like.

Alkyne moiety: A hydrocarbonr that has a triple bond between two carbon atoms, with the formula —$CCR_1$, where $R_1$ can be independently hydrogen, hydrocarbyl, substituted hydrocarbyl, substituted heterocyclo, alkyl, substituted alkyl, acyl, —C(O)R, —C(O)OR, or —$C(O)NR_aR_b$, aryl or substituted aryl or heterocyclic ring.

Alkyl: A linear, branched, or cyclic, hydrocarbon chain, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups.

The alkyl group can be optionally substituted with one or more alkyl group substituents which can be the same or different, where "alkyl group substituent" includes alkyl, halo, arylamino, acyl, hydroxy, aryloxy, alkoxyl, alkylthio, arylthio, aralkyloxy, aralkylthio, carboxy, alkoxycarbonyl, oxo and cycloalkyl. There can be optionally inserted along the alkyl chain one or more oxygen, sulfur or substituted or unsubstituted nitrogen atoms, wherein the nitrogen substituent is hydrogen, alkyl (also referred to herein as "alkylaminoalkyl"), or aryl. "Branched" refers to an alkyl group in which an alkyl group, such as methyl, ethyl or propyl, is attached to a linear alkyl chain.

Amino: The group —$NZ_1Z_2$, where each of $Z_1$ and $Z_2$ is independently selected from the group consisting of hydrogen; alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

Aptamer: Small nucleic acid and molecules that bind a specific target molecule, such as a target biomolecule, for example an analyte, such as a target analyte. In some examples, an aptamer is a CNA molecule.

Aryl: An aromatic substituent, which can be a single aromatic ring or multiple aromatic rings, which are fused together, linked covalently, or linked to a common group such as a methylene or ethylene moiety. The common linking group can also be a carbonyl as in benzophenone or oxygen as in diphenylether or nitrogen in diphenylamine. The aromatic ring(s) can include phenyl, naphthyl, biphenyl, diphenylether, diphenylamine and benzophenone among others. In particular embodiments, the term "aryl" means a cyclic aromatic comprising about 5 to about 10 carbon atoms, including 5- and 6-membered hydrocarbon and heterocyclic aromatic rings.

The aryl group can be optionally substituted with one or more aryl group substituents which can be the same or different, where "aryl group substituent" includes alkyl, aryl, aralkyl, hydroxy, alkoxyl, aryloxy, aralkoxyl, carboxy, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene and —NR'R", where R' and R" can be each independently hydrogen, alkyl, aryl and aralkyl.

Specific examples of aryl groups include but are not limited to cyclopentadienyl, phenyl, furan, thiophene, pyrrole, pyran, pyridine, imidazole, isothiazole, isoxazole, pyrazole, pyrazine, pyrimidine, and the like.

Binding or stable binding (of a CNA to an oligonucleotide): A CNA binds or stably binds to a target, such as a target nucleic acid, if a sufficient amount of the CNA forms base pairs or is hybridized to its target nucleic acid.

Binding can be detected by either physical or functional properties. Binding between a target and an oligonucleotide or CNA can be detected by any procedure known to one skilled in the art, including both functional (for example reduction in expression and/or activity) and physical binding assays.

Contacting: Placement in direct physical association including both in solid or liquid form, for example contacting a sample with a CNA. Contacting can occur in vitro, for example in a diagnostic assay, or in vivo, for example by administering an agent to a subject.

Covalent bond: An interatomic bond between two atoms, characterized by the sharing of one or more pairs of electrons by the atoms. The terms "covalently bound" or "covalently linked" refer to making two separate molecules into one contiguous molecule, for example a nucleobase and a CNA backbone, or a CNA molecule and a second molecule, such as an effector molecule.

Detectable label: A detectable molecule (also known as a label) that is conjugated directly or indirectly to a second molecule, such as a CNA molecule, to facilitate detection of the second molecule. For example, the detectable marker can be capable of detection by diagnostic imaging techniques (such as CT scans, MRIs, ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). Various methods of labeling polypeptides are known in the art and may be used.

Detect: To determine if an agent (such as a signal or particular CNA probe, or molecule bound be such a CNA probe) is present or absent. In some examples, this can further include quantification.

Effector molecule: A molecule intended to have or produce a desired effect, such as a therapeutic effect, detection, or other physical effect, such as but not limited to localization of the effector molecule. Effector molecules include such molecules as polypeptides, radioisotopes and small molecules (for example drugs) and labels.

Electron withdrawing group: Any substituent that draws electrons away from a vinyl bond. Exemplary electron withdrawing groups include hydroxy, alkoxy, mercapto, halogens, carbonyls, sulfonyls, nitrile, quaternary amines, nitro, trihalomethyl, imine, amidine, oxime, thioketone, thioester, or thioamide.

Epoxide: A cyclic ether with three ring atoms, in which two of the atoms are carbon and the remaining atom is oxygen bonded to the two carbons.

Halide or halo: An atom from the group of Br, Cl, I and F.

Heteroatom: An atom other than carbon. In some embodiments, the heteroatoms are selected from the group consisting of N, O, P, S, Si, B, Ge, Sn, and Se.

Heterocyclo or heterocyclic: An optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics as furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxyl, protected hydroxyl, acyl, acyloxy, alkoxy, alkenoxy, alkynoxy, aryloxy, halogen, amido, amino, nitro, cyano, thiol, ketals, acetals, esters and ethers.

Hybridization: Oligonucleotides and their analogs, such as CNAs. hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide (or it's analog, such as a CNA) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ concentration) of the hybridization buffer will determine the stringency of hybridization, though waste times also influence stringency.

Hydrocarbon or hydrocarbyl: Organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, as alkaryl, alkenaryl, and alkynaryl.

"Substituted hydrocarbyl", are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substitutents include halogen, heterocyclo, alkoxy, alkenoxy, alkynoxy, aryloxy, hydroxyl, protected hydroxy, keto, acyl, acyloxy, nitro, amino, amido, nitro, cyano, thiol, ketals, acetals, esters and ethers.

Label: A detectable compound or composition, which can be conjugated directly or indirectly to another molecule, such as a CNA, to facilitate detection of that molecule, or a molecule to which a CNA binds. Specific, non-limiting examples of labels include fluorescent tags, enzymes, and radioactive isotopes. Examples of labels include, but are not limited to, the following: radioisotopes or radionuclides (such as $^{35}S$ or $^{131}I$), fluorescent labels (such as fluoroscein istothiocyanate (FITC), rhodamine, lanthanide phosphors, cyanine dyes, fluorescent proteins, such as GFP), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms, such as linkers, of various lengths, for example to reduce potential steric hindrance.

Linker: A compound or moiety that acts as a molecular bridge to operably link two different molecules, wherein one portion of the linker is operably linked to a first molecule and wherein another portion of the linker is operably linked to a second molecule. There is no particular size or content limitations for the linker so long as it can fulfill its purpose as a molecular bridge. Linkers are known to those skilled in the art to include, but are not limited to, chemical chains, chemical compounds, carbohydrate chains, peptides, haptens and the like. In one embodiment, a linker links a nucleobase to the remainder of a CNA monomer. In another embodiment, a linker links a heterologous molecule, such as an effector molecule, to a CNA molecule.

Mimetic: A molecule (such as an organic chemical compound) that mimics the activity and/or structure of an agent, such as the activity of a nucleic acid, such as RNA and DNA. In one embodiment, a mimetic of a nucleic acid is a disclosed CNA.

Nucleobase: A nucleotide includes a nitrogen-containing base, which can be attached to a polymer backbone, such as a deoxyribonucleic, ribonucleic or thio-ether backbone among others.

The major nucleobases are adenosine (A), guanosine (G), cytidine (C), thymidine (T) uridine (U).

Nucleobases also include modified bases, for example as described in U.S. Pat. No. 5,866,336. Examples of modified base moieties include, but are not limited to: 5-fluorouracil, 5-bromouracil, 5-chlorouracil, 5-iodouracil, hypoxanthine, xanthine, acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N~6-sopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N2-carboxypropyl)uracil, and 2,6-diaminopurine amongst others.

Probe: A probe comprises an isolated nucleic acid or disclosed CNA capable of hybridizing to a target nucleic acid, and a detectable label or reporter molecule can be attached to a nucleic acid molecule. Typical labels include radioactive isotopes, enzyme substrates, co-factors, ligands, chemiluminescent or fluorescent agents, haptens, and enzymes.

Probes are generally at least 6 bases in length, such as at least 6, at least 7, at least 8, at least 9, least 10, at least 11, at least 12, at least 13, at least 14, at least 15, at least 16, at least 17, at least 18, at least 19, least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50 at least 51, at least 52, at least 53, at least 54, at least 55, at least 56, at least 57, at least 58, at least 59, at least 60, at least 70, at least 80, at least 90, at least 100, at least 120, at least 140, at least 160, at least 180, at least 200, at least 250, at least 300, at least 350, at least 400, at least 450, at least 500, or more contiguous bases complementary to the target nucleic acid molecule, such as 6-500 nucleotides, 20-400 nucleotides, 100-250 nucleotides, 20-40 nucleotides, or 20-30 nucleotides.

Pharmaceutically acceptable carriers: The pharmaceutically acceptable carriers (vehicles) useful in this disclosure are conventional. *Remington's Pharmaceutical Sciences*, by E. W. Martin, Mack Publishing Co., Easton, Pa., 19th Edition (1995), describes compositions and formulations suitable for pharmaceutical delivery of the nanoparticles disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Sample: A sample, such as a biological sample, is obtained from an animal subject, such as a human subject. As used herein, biological samples include all clinical samples, including, but not limited to, cells, tissues, and bodily fluids, such as: blood; derivatives and fractions of blood, tissue biopsy (including shave, punch, or excision biopsy of atypical or suspicious nevi) including tissues that are, for example, unfixed, frozen, fixed in formalin and/or embedded in paraffin. In some examples, a sample is one obtained from a subject having, suspected of having, or who has had, for example is diagnosed with melanoma, such as metastatic melanoma.

A polymer is a molecule with repeating general structural units (e.g., monomers, such as one or more disclosed CNA monomers) formed via a chemical reaction, e.g., polymerization.

Sequence identity/similarity: The identity/similarity between two or more nucleic acid sequences, nucleic acid sequence and a CNA sequences or two or more CNA sequences, is expressed in terms of the identity or similarity between the sequences. Sequence identity can be measured in terms of percentage identity; the higher the percentage, the more identical the sequences are.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene*, 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N80, Bethesda, Md. 20894) and on the Internet, for use in connection with the sequence analysis programs blastp, blastn, blastx, tblastn, and tblastx. Blastn is used to compare nucleic acid sequences, while blastp is used to compare amino acid sequences. Additional information can be found at the NCBI web site.

Once aligned, the number of matches is determined by counting the number of positions where an identical nucleotide or amino acid residue is present in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1554 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. One indication that two nucleic acid molecules and/or CNAs are closely related is that the two molecules hybridize to each other under stringent conditions.

Synthetic nucleic acids: Polymer molecules that include those constructed by joining nucleic acid containing molecules, for example nucleic acid molecules that are chemically or by other means synthesized or amplified, including those that are chemically or otherwise modified but can base pair with naturally occurring nucleic acid molecules, or with other synthetic nucleic acids. In one example, a synthetic nucleic acid id a CNA.

Click nucleic acids or CNAs, (molecule or sequence): A DNA and/or RNA mimetic polymer having a thio-ether backbone in place of the phosphate backbone typically found in DNA or RNA. The CNA can be double stranded (ds) or single stranded (ss) or even more, such as a triple helix. Where single stranded, the nucleic acid can be the sense strand or the antisense strand. CNA can include natural nucleobases (such as A, T/U, C, and G), and can include analogs of natural nucleobases, such as labeled nucleotides.

Thiol or thiol moiety or group: A carbon-bonded sulfhydryl (—C—SH or R—SH) group. In some examples, a thiol moiety is a protected thiol. Examples of thiol protecting groups are known in the art.

Thiol click chemistry: A reaction between a thiol moiety and thiol-click accepting group, such as a vinyl, alkyne, halide, isocyanate or epoxy moiety, achieved by one of many reaction mechanisms. Examples of thiol click chemistry reactions can be found in Hoyle et al. "Thiol-click chemistry: a multifaceted toolbox for small molecule and polymer synthesis", *Chemical Society Reviews* 39 (4) 1355-1387 (2010), which is specifically incorporated herein in its entirety.

Figure 18A:
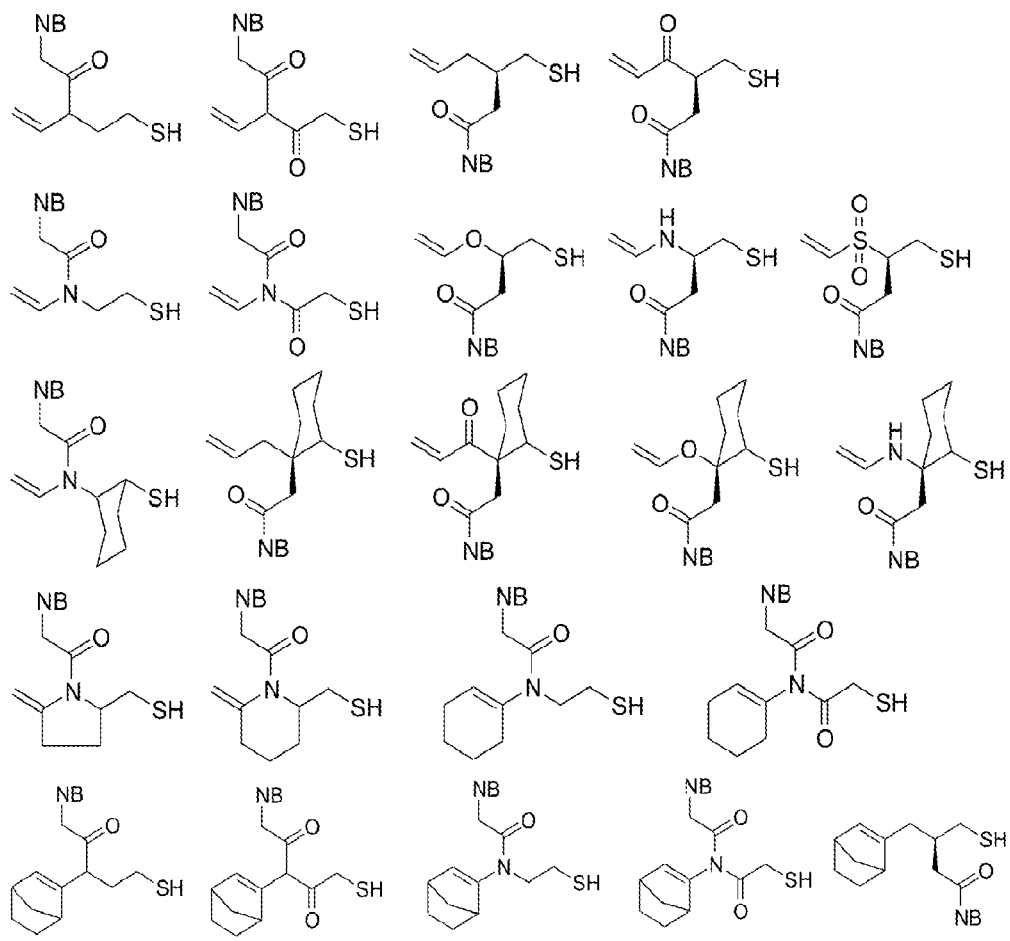
FIGS. 18A and 18B show exemplary non-protected CNA monomers, where NB is a nucleobase.
Figure 18B:
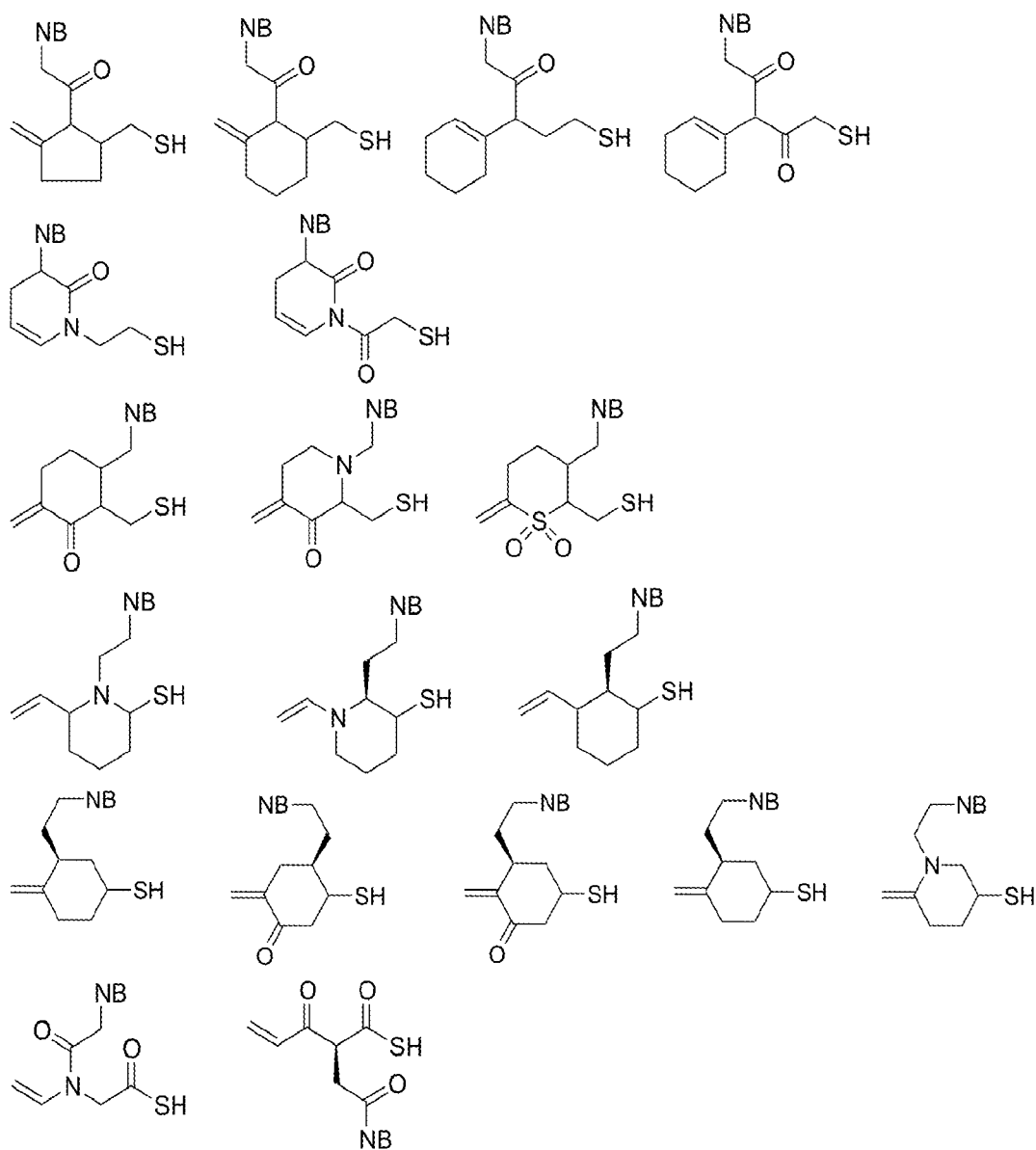

Thiol-click acceptor: A thiol-click acceptor is any chemical moiety that readily reacts with thiol, which may or may not contain a protecting group, to produce a thioether. Examples of such moieties are vinyl, vinyl ether, allyl ether, norbornene, vinyl sulfone, epoxy, acrylate, methacrylate, maleimide, halide and alkyl extensions thereof. Exemplary thiol-click acceptors can also be found in FIG. 18.

Vinyl moiety or vinyl group: A group having a carbon-carbon double bond, for example having the formula —$CR_1$=$CR_2R_3$, where $R_1$, $R_2$ and $R_3$ can be independently hydrogen, hydrocarbyl, substituted hydrocarbyl, substituted heterocyclo, alkyl, substituted alkyl, acyl, —C(O)R, —C(O)OR, or —C(O)$NR_aR_b$, aryl or substituted aryl or heterocyclic ring. In some examples, vinyl groups are part of allyl ethers, vinyl ethers, methacrylates, acrylate, maleimides, norbornenes, alpha-hydroxy methacrylates, vinyl sulfones, and the like. In some examples, a vinyl group is protected. Examples of vinyl protecting groups are known in the art.

Suitable methods and materials for the practice or testing of this disclosure are described below. Such methods and materials are illustrative only and are not intended to be limiting. Other methods and materials similar or equivalent to those described herein can be used.

II. Description of Exemplary Embodiments

A. Introduction

Disclosed are click nucleic acid (CNA) molecules, methods of making such molecules and the use thereof. As disclosed herein, the synergistic combination of thiol click chemistry with oligonucleotide synthesis creating novel CNA molecules has innumerable advantages and represents a significant innovation. While PNAs have demonstrated the vast utility of non-biological oligonucleotides, their synthetic approach, the limited backbone chemistries available, and the necessity for solid phase reactions severely limits their broad implementation. In contrast, the use of the click chemistry approaches, disclosed herein, enables the implementation of stoichiometric ratios of reactants and the simultaneous achievement of quantitative conversions has both great novelty and value. In particular, the simplicity, robustness, speed, and stoichiometric characteristics of the thiol-click chemistry reaction make it ideal for the development of a novel class of functional oligonucleotide mimetics. In fact, based on these advantages and chemical approach, initial polyCNA molecules have been readily produced on the 10 mg/batch scale at an estimated current cost of between $10-100/gram while the identical DNA sequence would cost almost $100,000/gram. This difference in cost renders CNAs as functional molecules in a vast array of applications for which DNA simply cannot be considered due to its great expense.

The thiol click chemistry approach enables several specific innovations when compared with either DNA or PNAs. Importantly, the quantitative yield from stoichiometric reactants facilitates the use of solution-based approaches to yield large volumes of controlled sequences at minimal cost. While a minimal amount of error may arise with this approach, simple purification via hybridization can result in isolation of the pure products.

As disclosed herein, reactive thiol-click acceptors, such as vinyl, vinyl ether, allyl ether, norbornene, vinyl sulfone, epoxy, acrylate, methacrylate, maleimide, halide and alkyl ene, alkyne, halide, isocyanate, epoxy, and thiol terminal groups are readily suited for further functionalization with various compounds such as PEGs for improving solubility, peptides, contrast agents and dyes, and/or other oligonucleotides, such as DNA or RNA. Further, the capability of further reaction is also the route to producing high molecular weight CNA sequences as purified, intermediate size 5, 10, or 20-mers of controlled sequence can be coupled in a single step to increase rapidly the number of bases in the sequence and achieve high molecular weights. Further, the robustness of the CNA approach enables the utilization of multiple basic monomer structures for creating CNAs. The click thio-ether nucleic acid monomers and polymers CNAs disclosed herein are substantially the same as thio-ether nucleic acid monomers and polymers TNAs disclosed in U.S. Provisional Application No. 61/617,145, filed on Mar. 29, 2012, to which a priority benefit is claimed. Only the nomenclature has been changed.

B. Click Nucleic Acids (CNAs)

Disclosed herein is a novel class of biofunctional oligonucleotides, thio-ether nucleic acids or CNAs, that utilize the thiol-ene 'click' reaction to form the desired base sequence. This approach, an example of which illustrated alongside DNA and PNA structures, is presented in FIG. 1, has several distinct advantages that enhance its significance, particularly, (i) the use of click chemistry, (ii) the capability to photoinitiate the reaction, and (iii) the formation of a polymer with a thio-ether backbone that will enhance the stability of the CNA molecules.

Disclosed herein are monomeric CNA molecules, structures or building blocks that can be used to create poly click nucleic acids. In some embodiments, a thio-ether nucleic acid monomer includes a an optionally protected thiol moiety, an optionally protected thiol-click acceptor, a optionally protected nucleobase and a backbone that includes an atom with a valency of 3 or more, such as carbon (C), nitrogen (N), or boron (B), and optionally additional atoms with a valency of 3 or more. The thiol moiety, the thiol reactive moiety and the nucleobase are covalently linked independently to the backbone. In some embodiments, the click nucleic acid monomer further includes a linker, wherein the linker covalently links the nucleobase to the atom with the valency of 3 or more. In some examples, the linker includes —C(O)C—. In some embodiments, the linker and the nucleobase are a nucleobase sidechain (NS). In some examples, the atom with a valency of 3 or more is a nitrogen (N) or carbon (C). In some examples, the amine of the nucleobase is protected, by a protecting group. Amine protecting groups are well known in the art. In some examples, the thiol group is protected. Thiol protecting groups are well known in the art. In some examples, the thiol is linked to the back bone atom by a sugar moiety.

In some embodiments, a click nucleic acid monomer has the following structure:

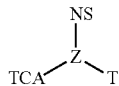

and Z is an atom having a valency of 3 or more, such as C, N, or B boron, NS is a nucleobase side-group, which includes an optionally protected nucleobase (NB) and optionally a linker, linking the NB and Z, T is thiol, which is optionally protected, and TCA is a thiol-click acceptor, which is optionally protected.

In some embodiments, a click nucleic acid backbone includes one or more additional atoms with a valency of 3 or more, such as C, N, or B.

In some embodiments, a click nucleic acid monomer has the structure:

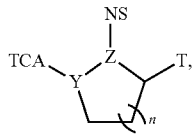

where Y and Z are atoms having a valency of 3 or more (for example carbon, nitrogen, and boron), n is an integer of from 0 to 4, such as 0, 1, 2, 3, or for, for example from 1-1, 0-2, 0-3, 0-4, 1-2, 1-3, 1-4, 2-3, 2-4, or 3-4, which may include heteroatoms and be independently substituted, for example with aryl, hydroxyl, carbonyl, carboxylic and other acids, amino, alkyl amide, thioether, cyclic, heterocyclic, and alkyl extensions thereof, NS is a nucleobase side-group, which includes an optionally protected nucleobase, T is an optionally protected thiol and TCA is an optionally protected thiol-click acceptor, such as optionally protected vinyl, vinyl ether, allyl ether, norbornene, vinyl sulfone, epoxy, acrylate, methacrylate, maleimide, halide and alkyl extensions thereof.

In some embodiments, a click nucleic acid monomer has the structure:

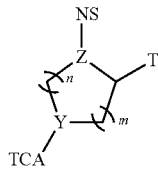

where Y and Z are atoms having a valency of 3 or more (for example carbon, nitrogen, and boron), n is an integer of from 0 to 4, such as 0, 1, 2, 3, or for, for example from 1-1, 0-2, 0-3, 0-4, 1-2, 1-3, 1-4, 2-3, 2-4, or 3-4, which may include heteroatoms and be independently substituted, for example with aryl, hydroxyl, carbonyl, carboxylic and other acids, amino, alkyl amide, thioether, cyclic, heterocyclic, and alkyl extensions thereof, m is an integer of from 0 to 4, such as 0, 1, 2, 3, or for, for example from 1-1, 0-2, 0-3, 0-4, 1-2, 1-3, 1-4, 2-3, 2-4, or 3-4, which may include heteroatoms and be independently substituted, for example with aryl, hydroxyl, carbonyl, carboxylic and other acids, amino, alkyl amide, thioether, cyclic, heterocyclic, and alkyl extensions thereof, NS is a nucleobase side-group, which includes an optionally protected nucleobase, T is an optionally protected thiol and TCA is an optionally protected thiol-click acceptor, such as optionally protected vinyl, vinyl ether, allyl ether, norbornene, vinyl sulfone, epoxy, acrylate, methacrylate, maleimide, halide and alkyl extensions thereof.

In some embodiments, a click nucleic acid monomer has the structure:

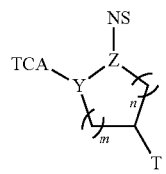

where Y and Z are atoms having a valency of 3 or more (for example carbon, nitrogen, and boron), n is an integer of from 0 to 4, such as 0, 1, 2, 3, or for, for example from 1-1, 0-2, 0-3, 0-4, 1-2, 1-3, 1-4, 2-3, 2-4, or 3-4, which may include heteroatoms and be independently substituted, for example with aryl, hydroxyl, carbonyl, carboxylic and other acids, amino, alkyl amide, thioether, cyclic, heterocyclic, and alkyl extensions thereof, m is an integer of from 0 to 4, such as 0, 1, 2, 3, or for, for example from 1-1, 0-2, 0-3, 0-4, 1-2, 1-3, 1-4, 2-3, 2-4, or 3-4, which may include heteroatoms and be independently substituted, for example with aryl, hydroxyl, carbonyl, carboxylic and other acids, amino, alkyl amide, thioether, cyclic, heterocyclic, and alkyl extensions thereof, NS is a nucleobase side-group, which includes an optionally protected nucleobase, T is an optionally protected thiol and TCA is an optionally protected thiol-click acceptor, such as optionally protected vinyl, vinyl ether, allyl ether, norbornene, vinyl sulfone, epoxy, acrylate, methacrylate, maleimide, halide and alkyl extensions thereof.

In some examples, tclick nucleic acid monomer has the following structure:

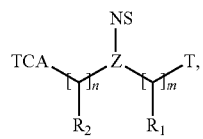

where n+m is between 1 and 7, such as 1, 2, 3, 4, 5, 6, or 7, n≥0, such as 0, 1, 2, 3, 4, 5, or 6 and m>0, such as 1, 2, 3, 4, 5, 6, or 7, NS is a nucleobase side group, including an optionally protected nucleobase, T is an optionally protected thiol and TCA is an optionally protected thiol-click acceptor, such as optionally protected vinyl, vinyl ether, allyl ether, norbornene, vinyl sulfone, epoxy, acrylate, methacrylate, maleimide, halide and alkyl extensions thereof, Z is the atom with a valency of 3 or more, and $R_1$ and $R_2$ are independently a combination of hydrogen, hydroxyl, aromatic, amine, carboxyl, and carbonyl groups, optionally substituted. In some examples, n+m is between 1 and 7, such as from 1-7, 1-6, 1-5, 1-4, 1-3, 1-2, 2-7, 2-6, 2-5, 2-4, 3-7, 3-6, 3-5, 3-4, 4-7, 4-6, 4-5, 5-6, 5-7, for example 1, 2, 3, 4, 5, 6, or 7. In some examples, n≥0, such as greater than or equal to 0, 1, 2, 3, 4, 5, or 6, for example, from 0-6, 0-5, 0-4, 0-3, 0-2, 0-1, 1-6, 1-5, 1-4, 1-3, 1-2, 2-7, 2-6, 2-5, 2-4, 3-6, 3-5, 3-4, 4-6, 4-5, or 5-6 and m>0, such as greater than 1, 2, 3, 4, 5, 6, or 7, for example from 1-7, 1-6, 1-5, 1-4, 1-3, 1-2, 2-7, 2-6, 2-5, 2-4, 3-7, 3-6, 3-5, 3-4, 4-7, 4-6, 4-5, 5-6, 5-7, In some embodiments, the click nucleic acid monomer further includes a linker, wherein the linker covalently links the nucleobase to the atom with the valency of 3 or more. In some examples, the linker includes —C(O)C—.

In some embodiments, an NS group has the structure:

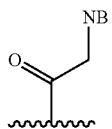

where NB is any nucleobase (for example A, T, G, C, or U), the amine on which may be protected.

In some embodiments, the optionally protected thiol has the structure:

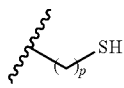

where p is an integer from 0 to 4, and wherein the methyl groups are optionally and independently substituted, for example substituted with aryl, hydroxyl, carbonyl, carboxylic and other acids, amino, alkyl amide, thioether, cyclic, heterocyclic, and alkyl extensions thereof. In a specific example, the optionally protected thiol has the structure:

In some embodiments a thiol-click acceptor is an optionally substituted vinyl, vinyl ether, allyl ether, norbornene, isocyanate, vinyl sulfone, epoxy, acrylate, methacrylate, maleimide, halide and alkyl extensions thereof. In specific examples, a thiol-click acceptor has the structure set forth as one of:

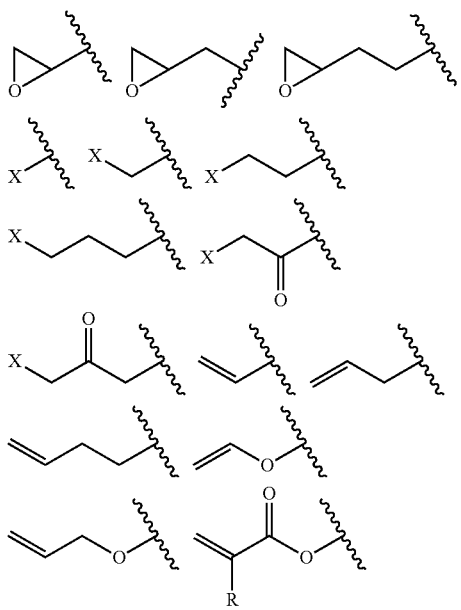

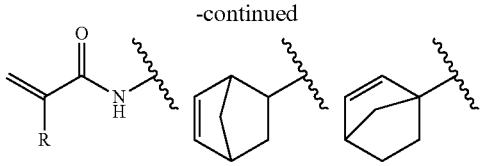

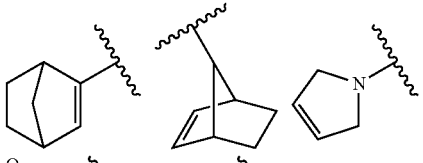

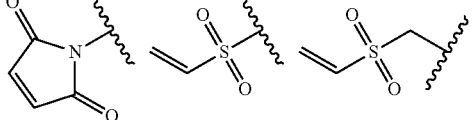

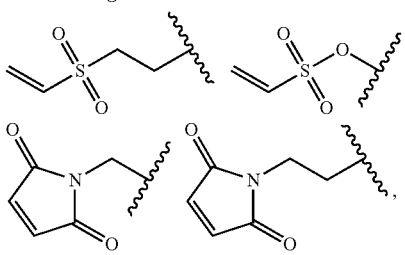

where X is a halide and R is a hydrogen or alkyl chain. In some examples, the thio-click acceptor is an acceptor moiety as shown in the monomers shown in FIGS. 18A and 18B.

In some examples, the click nucleic acid monomer includes an alkyne moiety. In some examples, the click nucleic acid monomer includes a halide moiety. In some examples, the click nucleic acid monomer includes an isocyanate moiety. In some examples, the click nucleic acid monomer includes an epoxy moiety. In some examples, the click nucleic acid monomer includes an acrylate moiety. In some examples, the click nucleic acid monomer includes a vinyl ether moiety. In some examples, a vinyl moiety (including the vinyl moieties in an acrylate or vinyl ether) has the structure —CR$_5$=CR$_6$R$_7$, wherein R$_5$, R$_6$, and R$_7$ can independently be hydrogen, aryl, hydroxyl, carbonyl, carboxylic and other acids, amino, alkyl amide, thioether, cyclic, heterocyclic, hydrocarbyl, substituted hydrocarbyl, substituted heterocyclo, alkyl, substituted alkyl, acyl, —C(O)R, —C(O)OR, or —C(O)NR$_a$R$_b$, aryl or substituted aryl or heterocyclic ring.

In some examples, a CNA monomer includes an electron withdrawing group, for example situated next to the vinyl group. While not being bound by theory, it is believed that such groups in proximity to a vinyl group lead to enhanced reactivity of the vinyl group. Examples of electron withdrawing group(s) include hydroxy, alkoxy, mercapto, halogen, carbonyl, sulfonyl, nitrile, quaternary amine, nitro, or trihalomethyl. In some examples, where the electron withdrawing group is alkoxy, it generally corresponds to the formula —OR where R is hydrocarbyl, substituted hydrocarbyl, or heterocyclo. In some examples, where the electron withdrawing group is mercapto, it generally corresponds to the formula —SR where R is hydrogen, hydrocarbyl, substituted hydrocarbyl or heterocyclo. In some examples, where the electron withdrawing group is a halogen atom, the electron withdrawing group may be fluoro, chloro, bromo, or iodo; typically, it will be fluoro or chloro. In some examples, where the electron withdrawing group is a carbonyl, it may be an aldehyde (—C(O)H), ketone (—C(O)R), ester (—C(O)OR), acid (—C(O)OH), acid halide (—C(O)X), amide (—C(O)NR$_a$R$_b$), or anhydride (—C(O)OC(O)R) where R is hydrocarbyl, substituted hydrocarbyl or heterocyclo, R$_a$ and R$_b$ are independently hydrogen, hydrocarbyl, substituted hydrocarbyl or heterocyclo, and X is a halogen atom. In some examples, where the electron withdrawing group is a sulfonyl, it may be an acid (—SO$_3$H) or a derivative thereof (—SO$_2$R) where R is hydrocarbyl, substituted hydrocarbyl or heterocyclo. In some examples, where the electron withdrawing group is a quaternary amine, it generally corresponds to the formula —N$^+$R$_a$R$_b$R$_c$ where R$_a$, R$_b$ and R$_c$ are independently hydrogen, hydrocarbyl, substituted hydrocarbyl or heterocyclo. In some examples, where the withdrawing group is a trihalomethyl, it is preferably trifluoromethyl or trichloromethyl.

Figure 13:
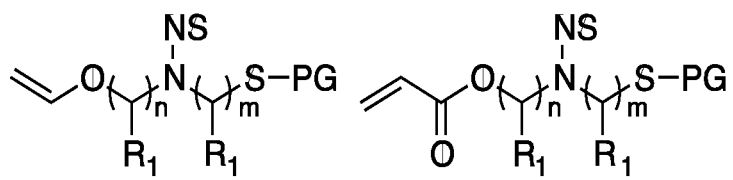
FIG. 13 shows the structures of vinyl ether- and acrylate-based CNA monomers, where n+m is between 1 and 7, and n>=0 and m>0, NS is a nucleobase side group, PG is a thiol protecting group (which may be removed). The $R_1$ side groups can be a combination of hydrogen, hydroxyl, aromatic, amine, carboxyl, and carbonyl functional groups.
Figure 14:
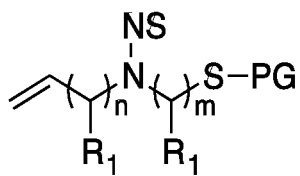
FIG. 14 shows a general structure of a monomer that incorporates the thiol-click reaction capability with the nucleobase side chain, where n+m is between 1 and 7, and n>=0 and m>0, NS is a nucleobase side group, PG is a thiol protecting group (which may be removed). The $R_1$ side groups can be a combination of hydrogen, hydroxyl, aromatic, amine, carboxyl, and carbonyl functional groups. $R_3$ is an atom with a valence of 3 or more, such as carbon or nitrogen.

In specific examples, a CNA monomer has a 5 to 7 atom repeat unit inclusive of the sulfur moiety and the terminal carbon of the vinyl moiety. In a specific example, the monomer has a 6-atom repeat unit inclusive of the thiol moiety and the terminal carbon of the vinyl moiety. In some embodiments, the CNA monomer has a N-vinyl thiol acetamide (VTA) backbone. In some embodiments, the monomer comprises a N-vinyl thiol ethylamine (VTE) backbone. In some embodiments, the monomer comprises a N-vinylether thiol backbone, wherein the vinyl moiety is linked to the remainder of the backbone through an ether linkage (see for example FIG. 13). In some embodiments, the monomer comprises a N-acrylate thiol backbone, where the reactive vinyl moiety is connected to the remainder of the backbone through a C(O)O group (see for example FIG. 13). In specific examples, a CNA has the structure of any of the CNA monomers shown in any one of FIGS. 4, 5 and/or 7-14, or 18, which can be protected. In some examples a CNA monomer is one of the monomers shown in FIG. 18A or 18B.

Figure 4:
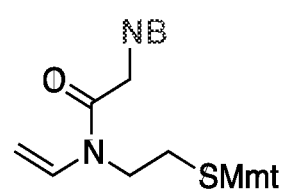
FIG. 4 shows a N-vinyl thiol ethylamine (VTE)-based CNA monomer structure. The base monomer contains a protected-thiol, vinyl, and nucleobase (NB) and has a 6-atom repeat unit.
Figure 15:
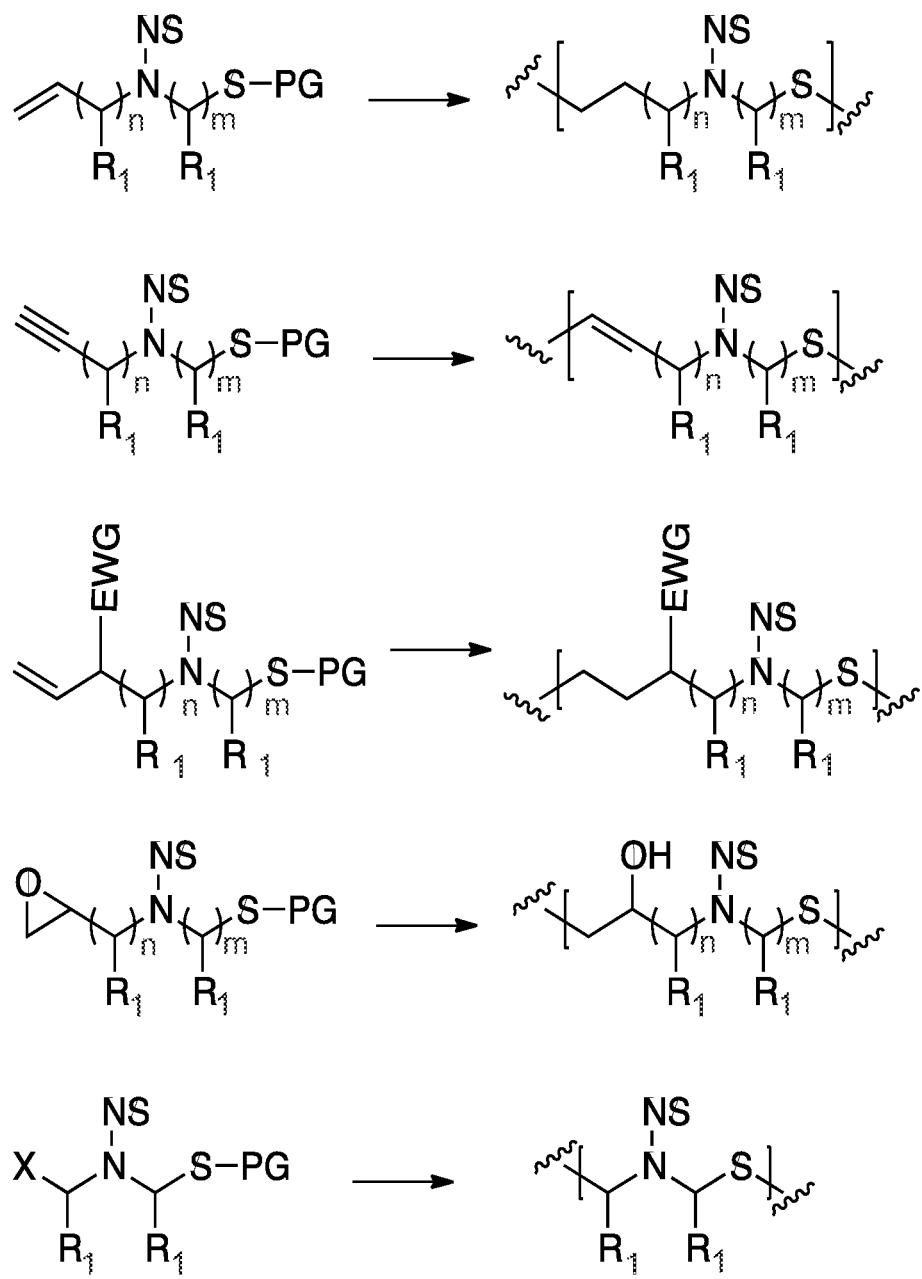
FIG. 15 shows the structures of exemplary monomers and their polymer products.

In some examples the CNA monomers include an A, G, T, U, or C nucleobase, although other nucleobases are contemplated, such as but not limited to those recited above in the listing of terms. As shown in FIG. 4, an exemplary monomer contains a six atom repeating unit. In some embodiments, a CNA monomer has a 3-10, atom repeating unit spacing, such as a 3, 4, 5, 6, 7, 8, 9, 10 or even longer repeating unit spacing, such, 5-9, 5-7-atom repeat unit spacing, for example inclusive of sulfur atom of the thiol and terminal carbon of the TCA group, (see for example FIG. 15).

It is contemplated that the disclosed monomers can be further modified, for example, to address any instability, toxicity, backbone stiffness, electronic charge, or solubility issues, for example, the basic monomer structure can be altered to facilitate, for example, the addition of anionic moieties to mimic better the DNA structure or by changing the number of backbone repeat unit atoms to optimize hybridization selectivity. In addition, the thiol and thiol-click acceptors moieties can be readily functionalized to add additional substituents, such as effector molecules, such as PEGs for improving solubility, peptides, contrast agents and dyes, and/or other oligonucleotides, such as DNA or RNA.

Disclosed are CNA, polymers and methods of producing a CNA polymer. A CNA polymer, includes at least two of the disclosed CNA monomer. The polymers can be of any length. The CNA polymers can be homogenous, or hetrogenous, for example a polymer can be composed of a single type of disclosed monomer or any combination of monomers disclosed herein.

Effector molecules, such as therapeutic, diagnostic, or detection moieties or others molecules can be linked a CNA molecule, using any number of means known to those of skill in the art. Both covalent and noncovalent attachment means may be used. The procedure for attaching an effector molecule to a CNA molecule according to the chemical structure of the effector and which end of the CNA molecule attachment is to occur. For example Polypeptides typically contain a variety of functional groups; e.g., carboxylic acid (COOH), free amine (—NH$_2$) or sulfhydryl (—SH) groups, which are available for reaction with a suitable functional group (for example the thiol or TCA moiety present on either end of the CNA molecule) on the CNA molecule result in the binding of the effector molecule. This attachment can be direct or through a linker and may involve attachment of any of a number of linker molecules such as those available from Pierce Chemical Company, Rockford, Ill. The linker can be any molecule used to join the CNA molecule to the effector molecule. The linker is capable of forming covalent bonds to both CNA molecule and to the effector molecule. Suitable linkers are well known to those of skill in the art and include, but are not limited to, straight or branched-chain carbon linkers, heterocyclic carbon linkers, or peptide linkers.

In some circumstances, it is desirable to free the effector molecule from the CNA molecule. Therefore, in these circumstances, such conjugates will comprise linkages that are cleavable.

In view of the large number of methods that have been reported for attaching a variety of radiodiagnostic compounds, radiotherapeutic compounds, label (e.g. enzymes or fluorescent molecules) drugs, toxins, and other agents, one skilled in the art will be able to determine a suitable method for attaching a given agent to an CNA molecule.

Figure 5:
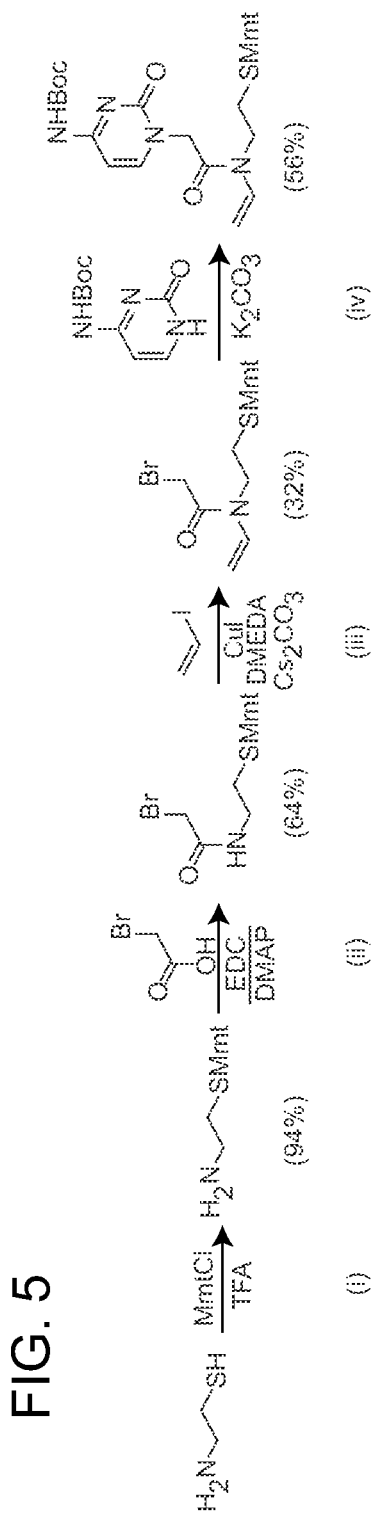
FIG. 5 is a schematic showing the synthesis of the cytosine-CNA monomer (C-CNA). CNA monomer synthesis begins with thiol protection with a methoxytrityl group (step i) and proceeds via amide coupling of bromoacetic acid (step ii) followed by vinyl group addition to the secondary amine (step iii). Cytosine is Boc protected and coupled to pendant bromoacetamide (step iv) to form the protected product. All products were confirmed by NMR and percentages are the preliminary (i.e., non-optimized) yields for each step.
Figure 8:
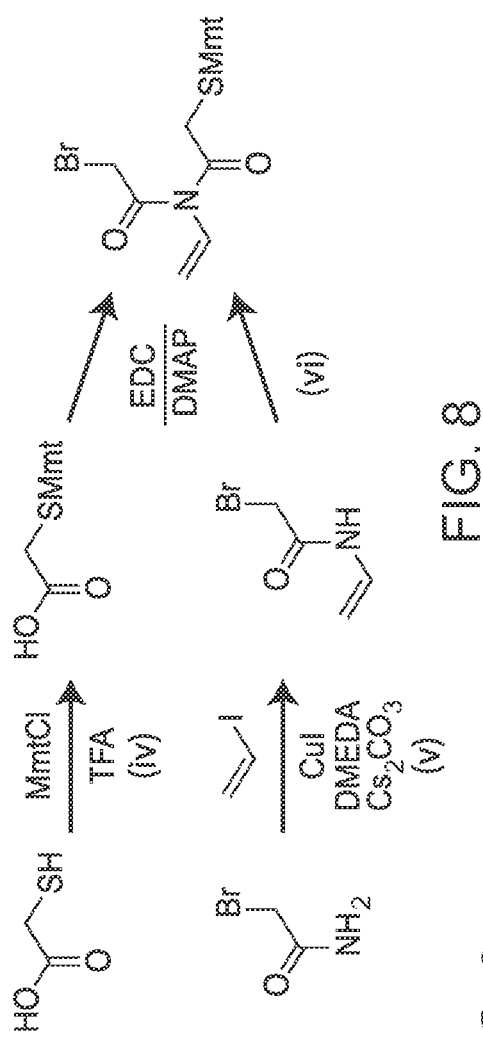
FIG. 8 shows a synthetic scheme of N-vinyl thiol acetamide (VTA)-based CNA monomer. The thiol of mecaptoacetate is protected using a methoxytrityl group (step iv) while a vinyl group is added to the bromoacetamide (step v). The two products are carbodiimide coupled (step vi) to form the CNA with a pendant bromoacetamide to which the nucleobase is added.

Disclosed herein are methods of producing a CNA monomer. One example of a method of producing a N-vinyl thiol ethylamine (VTE) based CNA monomer is shown in FIG. 5. One example of a method of producing a N-vinyl thiol acetamide (VTA) based CNA monomer is shown in FIG. 8. In both examples, the CNA monomer is synthesized from several simple molecular constituents, allowing precise, atomic level monomer design. Having this synthetic control over the monomer structure further enables simple structural variations as a possible contingency of poor solubility or hybridization efficiency or as further optimization of hybridization stability. As shown in FIG. 5, a CNA monomer is synthesized using three coupling reactions: thiol protection using a methoxytrityl group (Mmt), amide coupling, and vinyl iodide reaction with amide. As shown in FIG. 5, the last step of coupling the cytosine to the bromoacetic acid is readily extended to the remaining three nucleobases (adenine, thymine, and guanine) to make all CNA analogs of DNA.

Disclosed are CNA, polymers and methods of producing a CNA polymer. A CNA polymer, includes at least two of the disclosed CNA monomer. The polymers can be of any length. The CNA polymers can be homogenous, or hetrogenous, for example a polymer can be composed of a single type of disclosed monomer or any combination of monomers disclosed herein.

Figure 2:
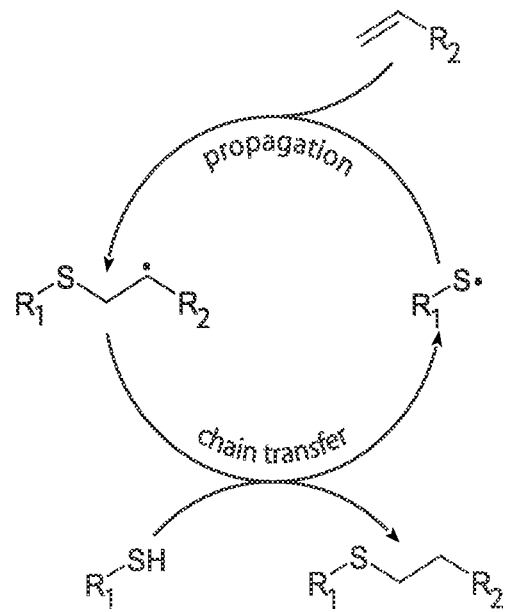
Figure 3:
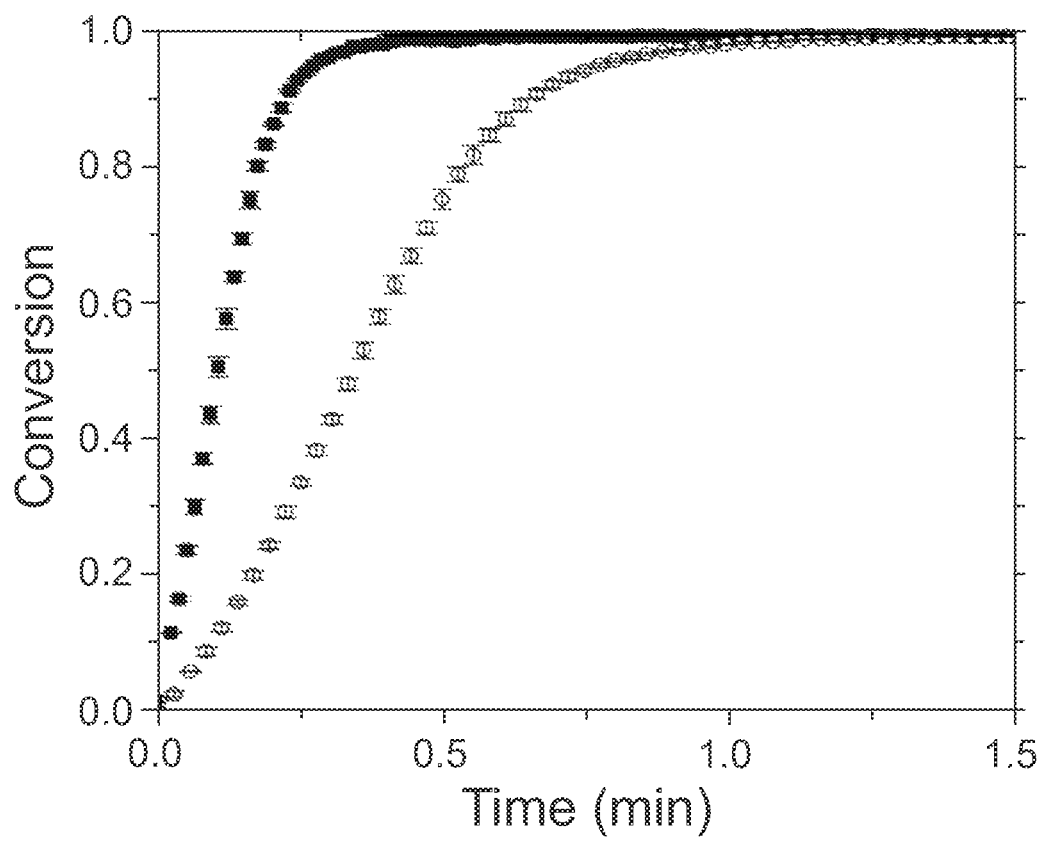
FIG. 3 shows functional group conversion for two thiol-ene photopolymerization reactions, demonstrating complete conversion. Shown is the 'ene' conversion for the polymerization of stoichiometric mixtures of trivinyl ether and dithiol monomers (left) and triallyl ether and dithiol monomers (right). While not shown, the thiol conversions follow identical conversion profiles, indicating one-to-one reaction kinetics between ene and thiol. This result demonstrates the ease and rapidity with which thiol-ene reactions of stoichiometric mixtures achieve complete conversion of the reactants as critical to many of the proposed implementations described herein. The reactions where photoinitiated with 0.1 wt % hydroxy-cyclohexyl-phenyl-ketone at 10 mW/cm² with 365 nm light.
Figure 9:
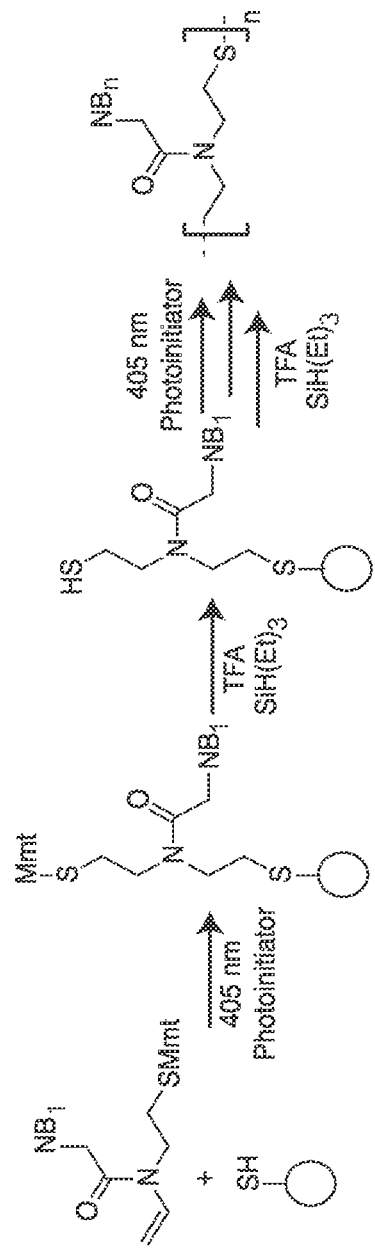
FIG. 9 shows synthesis of CNA utilizing a solid substrate. The nucleobase (NB) group is unaffected by the thiol-ene coupling, which is performed using visible light and photoinitiator, followed by removal of the Mmt protecting group. This process is repeated to produce CNAs with multiple nucleobases ($NB_x$) and then cleaved from the substrate yielding the CNA product.
Figure 10:
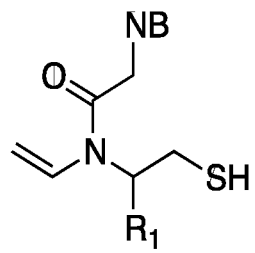
FIG. 10 shows a Base CNA monomer structure, where $R_1$ is hydrogen (H) or carbonyl (=O) for VTE and VTA, respectively.
Figure 11:
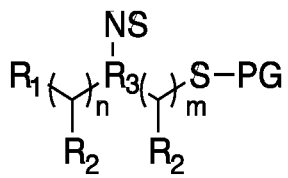
FIG. 11 shows a general structure of an exemplary CNA monomer that incorporates the thiol-click reaction capability with the nucleobase side chain, where n+m is between 1 and 7, and n>=0 and m>0, NS is a nucleobase side group, PG is a thiol protecting group (which may be removed), and $R_1$ can be a thiol-click acceptor, such as a vinyl, alkyne, halide, isocyanate, or epoxy and the like. The $R_2$ side groups can be a combination of hydrogen, hydroxyl, aromatic, amine, carboxyl, and carbonyl functional groups. $R_3$ is an atom with a valence of 3 or more, such as carbon or nitrogen.
Figure 12:
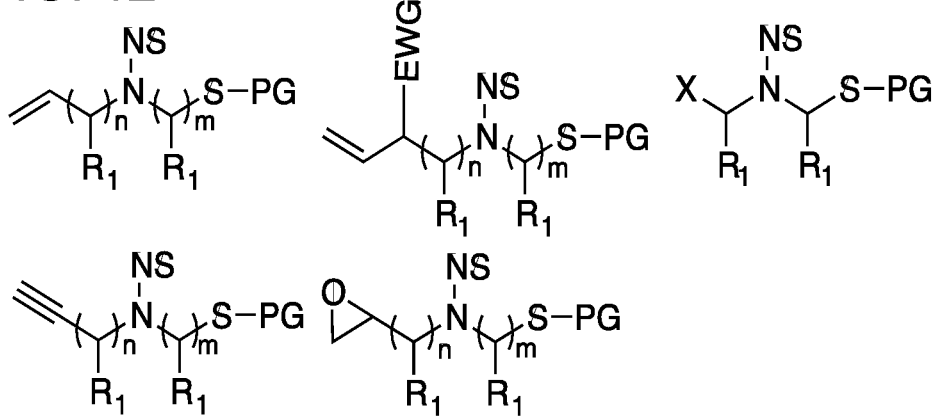
FIG. 12 shows the structures of exemplary monomers, as described in the FIG. 11, where n+m is between 1 and 7, and n>=0 and m>0, NS is a nucleobase side group, PG is a thiol protecting group, EWG is an electron withdrawing group, which can optionally be included. The $R_1$ side groups can be a combination of hydrogen, hydroxyl, aromatic, amine, carboxyl, and carbonyl functional groups.

Disclosed herein are methods of producing CNA polymers. To create CNA polymers, the CNA monomers are polymerized through a variety of methods including solid-phase, in solution, in microarray-style formats, and in bulk polymerization to generate homopolymers. An example of CNA polymerization is shown in FIG. 2. As shown in FIG. 2, the thiol of monomeric CNA is deprotected to expose the thiol moiety. Through a photoinitiated radical reaction, for example using the hydroxy-cyclohexyl-phenyl-ketone with 365 nm light, a radical is formed on the thiol, which can then proceed to attack a either a vinyl ether or allyl ether of the next monomer in the propagating chain. Through this mechanism, a CNA polymer is formed. An example of solid-phase formation of a CNA polymer is shown in FIG. 9. In analogy to solid-phase peptide synthesis, through rounds successive reaction with monomer and deprotection of the monomer added to the growing polymer chain, any nucleobase can be added to the growing chain.

In some examples the polymerization reaction is photoinitiated. The reactions can be photoinitiated with a photoinducible photoactivator, for example with hydroxy-cyclohexyl-phenyl-ketone. In some examples, the reaction is photoinitiated with between about 0.001 wt % and about 1.0% hydroxy-cyclohexyl-phenyl-ketone, such as about 0.01 wt % hydroxy-cyclohexyl-phenyl-ketone, 0.01 wt % hydroxy-cyclohexyl-phenyl-ketone or 1.0 wt % hydroxy-cyclohexyl-phenyl-ketone. In some examples, the photoactivator is activated at about 1 to about 100 mW/cm$^2$ light having a wavelength between about 350 and 410 nm. In a specific example, the photoactivator is activated with light of about 10 mW/cm$^2$ with a wavelength of about 365 nm.

The ability to photoinitiate the reaction is of great innovation. With this capability, arrays of sequences (akin to the Affymetrix DNA chips) are readily produced on a single chip in a facile manner for biodetection, origami, or other applications.

C. Exemplary Methods of Use i. Exemplary In Vitro CNA Applications

CNA applications include biodetection, development of a SELEX-like process, and replication of complementary DNA or CNA sequences. Targeting similar amplification and outcomes as PCR, an exponential amplification process through which CNA strands are replicated from complementary DNA or CNA strands by in situ hybridization and selective ligation of oligomeric CNAs. This process will function as one means of producing large volumes of high molecular weight sequences and be appropriate for implementation in biodetection, where substrate amplification is critical to detection.

a. Probes and Primers

The disclosed CNA molecules can be used as probes and/or primers capable of binding to and detecting a target nucleic acid. Typically, such probes and primers are between 6 and 40 nucleotides in length, such as 6, 7, 8, 9, 10, 11, 12, 13, 14, 15, 16, 17, 18, 19, 20, 21, 22, 23, 24, 25, 26, 27, 28 29, 30, 31, 32, 32, 34, 35, 36, 37, 38, 39, or 40 nucleotides in length and are capable of hybridizing a target nucleic acid, although longer and/or shorter sequences are contemplated, for example for southern blots and other applications. Thus in some examples, a probe or primer is greater that 40 nucleotides in length, such as at least 50 nucleotides, at least 60 nucleotides, at least 70 nucleotides, at least 80 nucleotides, at least 90 nucleotides, at least 100 nucleotides, at least 150 nucleotides, at least 200 nucleotides, at least 250 nucleotides, at least 500 nucleotides, or even at least 1000 nucleotides in length.

In some embodiments, a CNA probe and/or primer is detectably labeled, either with an isotopic or non-isotopic label, alternatively the target nucleic acid (such as an influenza nucleic acid) is labeled. Non-isotopic labels can, for instance, comprise a fluorescent or luminescent molecule, biotin, an enzyme or enzyme substrate or a chemical. Such labels are preferentially chosen such that the hybridization of the probe with target nucleic acid can be detected. In some examples, the probe is labeled with a fluorophore. In some examples, a CNA molecule, such as a probe, is linked to a solid substrate, such as a bead and/or an array.

b. Detection and Identification of a Target Nucleic Acid

A major application of the CNA molecules primers and probes disclosed herein is for the detection of a target nucleic acid in a sample, such as a biological sample. The methods described herein may be used for any purpose where the detection of a target nucleic acid is desirable, including diagnostic and prognostic applications, such as in laboratory and clinical settings. Appropriate samples include any conventional environmental or biological samples, including clinical samples obtained from a human or veterinary subject, including, but not limited to, cells, tissues (for example, lung, liver and kidney), bone marrow aspirates, bodily fluids (for example, blood, serum, urine, cerebrospinal fluid, bronchioalveolar levage, tracheal aspirates, sputum, nasopharyngeal aspirates, oropharyngeal aspirates, saliva), eye swabs, cervical swabs, vaginal swabs, rectal swabs, stool, and stool suspensions.

c. CNA Arrays

Also disclosed are arrays containing a plurality of homogeneous or heterogeneous CNA probes for the detection of target nucleic acids. Arrays are arrangements of addressable locations on a substrate, with each address containing a CNA, such as a probe. In some embodiments, each address corresponds to a single type or class of CNA, such as a single probe, though a particular CNA may be redundantly contained at multiple addresses. A "microarray" is a miniaturized array requiring microscopic examination for detection of hybridization. Larger "macroarrays" allow each address to be recognizable by the naked human eye and, in some embodiments, a hybridization signal is detectable without additional magnification. The addresses may be labeled, keyed to a separate guide, or otherwise identified by location.

Any sample potentially containing, or even suspected of containing, a target nucleic acid, including nucleic acid extracts, such as amplified or non-amplified DNA or RNA preparations may be targeted and analyzed. A hybridization signal from an individual address on the array indicates that the probe hybridizes to a nucleotide within the sample. This system permits the simultaneous analysis of a sample by plural probes and yields information identifying the influenza nucleic acids contained within the sample.

The nucleic acids may be added to an array substrate in dry or liquid form. Other compounds or substances may be added to the array as well, such as buffers, stabilizers, reagents for detecting hybridization signal, emulsifying agents, or preservatives.

Within an array, each arrayed CNA is addressable, such that its location may be reliably and consistently determined within the at least the two dimensions of the array surface. Thus, ordered arrays allow assignment of the location of each nucleic acid at the time it is placed within the array. Usually, an array map or key is provided to correlate each address with the appropriate nucleic acid. Ordered arrays are often arranged in a symmetrical grid pattern, but nucleic acids could be arranged in other patterns (for example, in radially distributed lines, a "spokes and wheel" pattern, or ordered clusters). Addressable arrays can be computer readable; a computer can be programmed to correlate a particular address on the array with information about the sample at that position, such as hybridization or binding data, including signal intensity. In some exemplary computer readable formats, the individual samples or molecules in the array are arranged regularly (for example, in a Cartesian grid pattern), which can be correlated to address information by a computer.

d. Nucleic Acid "Origami" and Directed Assembly

The disclosed CNA molecules can be used in nucleic acid origami and directed assembly applications, for example as a nucleic acid staple. Nucleic acid origami is the nanoscale folding of nucleic acids to create arbitrary two and three-dimensional shapes at the nanoscale. The specificity of the interactions between complementary base pairs make DNA a useful construction material, through design of its base sequences. Nucleic acid origami involves the folding of a long single strand of viral DNA aided by multiple smaller "staple" strands. In some examples, images are drawn with a raster full of a single long DNA molecule. This design is then fed into a computer program that calculates the placement of individual staple strands. Each staple binds to a specific region of the DNA template, and thus due to Watson-Crick base pairing, the necessary sequences of all staple strands are known and displayed. The DNA is mixed, then heated and cooled. As the DNA cools, the various staples pull the long strand into the desired shape. Designs are directly observable via several methods, including atomic force microscopy, or fluorescence microscopy when DNA is coupled to fluorescent materials Such self-assembly of nucleic acid can be used for synthesis of nanostructures under relatively mild conditions, for applications such as enzyme immobilization, drug carry capsules, and nanotechnological self-assembly and directed patterning of materials on surfaces and in the bulk solution or suspension, for example nanoparticles with desired characteristics.

ii. In Vivo CNA Applications

In light of their unique chemical and physical properties, CNAs have considerable potential for in vivo applications. Of interest is the potential for CNAs to transverse the outer cell membrane. Given CNAs hydrophobicity and neutral backbone, CNAs will penetrate the lipid membrane of cells and have intrinsically high cell permeability. Importantly, the ability of CNAs to enter cells can be optimized by chemically tailoring the liphophilicity of the CNA monomers. This ability, combined with the in vivo stability and high affinity and specificity of CNAs towards complementary RNA and DNA is exploited for RNA and/or DNA interference. Specifically, CNAs will be used to silence target genes and entire pathways. This use has broad implications for therapeutics and for mechanistic studies involving gene regulation. Moreover, this cell-penetrating ability is useful for delivery of exogenous dyes or therapeutic molecules, including proteins.

a. Therapeutic Compositions

The disclosed CNA polymers can be administered in vivo to a cell or subject. Generally, it is desirable to prepare the compositions as pharmaceutical compositions appropriate for the intended application. Accordingly, methods for making a medicament or pharmaceutical composition containing the CNAs as described herein above are included. Typically, preparation of a pharmaceutical composition (medicament) entails preparing a pharmaceutical composition that is essentially free of pyrogens, as well as any other impurities that could be harmful to humans or animals. Typically, the pharmaceutical composition contains appropriate salts and buffers to render the components of the composition stable and allow for uptake by target cells, such as tumor cells.

Therapeutic compositions can be provided as parenteral compositions, such as for injection or infusion. Such compositions are formulated generally by mixing a disclosed therapeutic agent at the desired degree of purity, in a unit dosage injectable form (solution, suspension, or emulsion), with a pharmaceutically acceptable carrier, for example one that is non-toxic to recipients at the dosages and concentrations employed and is compatible with other ingredients of the formulation. In addition, a disclosed therapeutic agent can be suspended in an aqueous carrier, for example, in an isotonic buffer solution at a pH of about 3.0 to about 8.0, preferably at a pH of about 3.5 to about 7.4, 3.5 to 6.0, or 3.5 to about 5.0. Useful buffers include sodium citrate-citric acid and sodium phosphate-phosphoric acid, and sodium acetate/acetic acid buffers. The active ingredient, optionally together with excipients, can also be in the form of a lyophilisate and can be made into a solution prior to parenteral administration by the addition of suitable solvents. Solutions such as those that are used, for example, for parenteral administration can also be used as infusion solutions.

Pharmaceutical compositions can include an effective amount of the CNA dispersed (for example, dissolved or suspended) in a pharmaceutically acceptable carrier or excipient. Pharmaceutically acceptable carriers and/or pharmaceutically acceptable excipients are known in the art and are described, for example, in *Remington's Pharmaceutical Sciences*, by E. W. Martin, Mack Publishing Co., Easton, Pa., 19th Edition (1995).

The nature of the carrier will depend on the particular mode of administration being employed. For example, parenteral formulations usually contain injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch or magnesium stearate. In addition, pharmaceutical compositions to be administered can contain minor amounts of non-toxic auxiliary substances, such as wetting or emulsifying agents, preservatives, and pH buffering agents and the like, for example sodium acetate or sorbitan monolaurate.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the pharmaceutical compositions is contemplated. Supplementary active ingredients also can be incorporated into the compositions. For example, certain pharmaceutical compositions can include the CNA in water, mixed with a suitable surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

Administration of therapeutic compositions can be by any common route as long as the target tissue is available via that route. This includes oral, nasal, ocular, buccal, or other mucosal (such as rectal or vaginal) or topical administration. Alternatively, administration will be by orthotopic, intradermal subcutaneous, intramuscular, intraperitoneal, or intravenous injection routes. Such pharmaceutical compositions are usually administered as pharmaceutically acceptable compositions that include physiologically acceptable carriers, buffers or other excipients.

The pharmaceutical compositions can also be administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain about 100 mg of human serum albumin per milliliter of phosphate buffered saline. Other pharmaceutically acceptable carriers include aqueous solutions, non-toxic excipients, including salts, preservatives, buffers and the like may be used. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components of the pharmaceutical composition are adjusted according to well known parameters.

Additional formulations are suitable for oral administration. Oral formulations can include excipients such as, pharmaceutical grades of mannitol, lactose, starch, magnesium stearate, sodium saccharine, cellulose, magnesium carbonate and the like. The compositions (medicaments) typically take the form of solutions, suspensions, aerosols or powders.

When the route is topical, the form may be a cream, ointment, salve or spray. An effective amount of the pharmaceutical composition is determined based on the intended goal, for example vaccination of a human or non-human subject. The appropriate dose will vary depending on the characteristics of the subject, for example, whether the subject is a human or non-human, the age, weight, and other health considerations pertaining to the condition or status of the subject, the mode, route of administration, and number of doses, and whether the pharmaceutical composition includes CNA.

When administering an nucleic acid, facilitators of nucleic acid uptake and/or expression can also be included, such as bupivacaine, cardiotoxin and sucrose, and transfection facilitating vehicles such as liposomal or lipid preparations that are routinely used to deliver nucleic acid molecules. Anionic and neutral liposomes are widely available and well known for delivering nucleic acid molecules (see, for example, *Liposomes: A Practical Approach*, RPC New Ed., IRL Press, 1990). Cationic lipid preparations are also well known vehicles for use in delivery of nucleic acid molecules. Suitable lipid preparations include DOTMA (N-[1-(2,3-dioleyloxy)propyl]-N,N,N-trimethylammonium chloride), available under the tradename LIPOFECTIN®, and DOTAP (1,2-bis(oleyloxy)-3-(trimethylammonio)propane). See, for example, Felgner et al., *Proc. Natl. Acad. Sci. U.S.A.* 84:7413-7416, 1987; Malone et al., *Proc. Natl. Acad. Sci. U.S.A.* 86:6077-6081, 1989; U.S. Pat. Nos. 5,283,185 and 5,527,928, and International Publication Nos. WO 90/11092, WO 91/15501 and WO 95/26356. These cationic lipids may preferably be used in association with a neutral lipid, for example DOPE (dioleyl phosphatidylethanolamine). Still further transfection-facilitating compositions that can be added to the above lipid or liposome preparations include spermine derivatives (see, for example, International Publication No. WO 93/18759) and membrane-permeabilizing compounds such as GALA, Gramicidine S and cationic bile salts (see, for example, International Publication No. WO 93/19768).

An appropriate effective amount can be readily determined by one of skill in the art. Such an amount will fall in a relatively broad range that can be determined through routine trials, for example within a range of about 10 µg to about 1 mg. However, doses above and below this range may also be found effective.

Therapeutic compositions that include a disclosed therapeutic agent can be delivered by way of a pump (see Langer, supra; Sefton, *CRC Crit. Ref Biomed. Eng.* 14:201, 1987; Buchwald et al., *Surgery* 88:507, 1980; Saudek et al., *N. Engl. J. Med.* 321:574, 1989) or by continuous subcutaneous infusions, for example, using a mini-pump. An intravenous bag solution can also be employed. One factor in selecting an appropriate dose is the result obtained, as measured by the methods disclosed here, as are deemed appropriate by the practitioner. Other controlled release systems are discussed in Langer (*Science* 249:1527-33, 1990).

In one example, a pump is implanted (for example see U.S. Pat. Nos. 6,436,091; 5,939,380; and 5,993,414). Implantable drug infusion devices are used to provide patients with a constant and long-term dosage or infusion of a therapeutic agent. Such device can be categorized as either active or passive.

Active drug or programmable infusion devices feature a pump or a metering system to deliver the agent into the patient's system. An example of such an active infusion device currently available is the Medtronic SYN-CHROMED™ programmable pump. Passive infusion devices, in contrast, do not feature a pump, but rather rely upon a pressurized drug reservoir to deliver the agent of interest. An example of such a device includes the Medtronic ISOMED™.

In particular examples, therapeutic compositions including a disclosed therapeutic agent are administered by sustained-release systems. Suitable examples of sustained-release systems include suitable polymeric materials (such as, semi-permeable polymer matrices in the form of shaped articles, for example films, or microcapsules), suitable hydrophobic materials (for example as an emulsion in an acceptable oil) or ion exchange resins, and sparingly soluble derivatives (such as, for example, a sparingly soluble salt). Sustained-release compositions can be administered orally, parenterally, intracistemally, intraperitoneally, topically (as by powders, ointments, gels, drops or transdermal patch), or as an oral or nasal spray. Sustained-release matrices include polylactides (U.S. Pat. No. 3,773,919, EP 58,481), copolymers of L-glutamic acid and gamma-ethyl-L-glutamate (Sidman et al., *Biopolymers* 22:547-556, 1983, poly(2-hydroxyethyl methacrylate)); (Langer et al., *J. Biomed. Mater. Res.* 15:167-277, 1981; Langer, *Chem. Tech.* 12:98-105, 1982, ethylene vinyl acetate (Langer et al., Id.) or poly-D-(−)-3-hydroxybutyric acid (EP 133,988).

Polymers can be used for ion-controlled release. Various degradable and nondegradable polymeric matrices for use in controlled drug delivery are known in the art (Langer, *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; and Pec, *J. Parent. Sci. Tech.* 44(2):58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa., 1993). Numerous additional systems for controlled delivery of therapeutic proteins are known (for example, U.S. Pat.

No. 5,055,303; U.S. Pat. No. 5,188,837; U.S. Pat. No. 4,235,871; U.S. Pat. No. 4,501,728; U.S. Pat. No. 4,837,028; U.S. Pat. No. 4,957,735; and U.S. Pat. No. 5,019,369; U.S. Pat. No. 5,055,303; U.S. Pat. No. 5,514,670; U.S. Pat. No. 5,413,797; U.S. Pat. No. 5,268,164; U.S. Pat. No. 5,004,697; U.S. Pat. No. 4,902,505; U.S. Pat. No. 5,506,206; U.S. Pat. No. 5,271,961; U.S. Pat. No. 5,254,342; and U.S. Pat. No. 5,534,496).

A disclosed CNA can also be conjugated with a detectable marker. For example, a detectable marker capable of detection by a diagnostic imaging techniques (such as CT scans, MRIs, ultrasound, fiberoptic examination, and laparoscopic examination). Specific, non-limiting examples of detectable markers include radioactive isotopes and heavy metals or compounds (for example super paramagnetic iron oxide nanocrystals for detection by MRI). Means of detecting such detectable markers are well known to those of skill in the art. Thus, for example, radiolabels may be detected using photographic film or scintillation counters.

The pharmaceutical compositions can be administered to the subject in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the compound can be provided as repeated doses within a prolonged prophylaxis or treatment regimen that will yield clinically significant results, for example to alleviate one or more symptoms or detectable conditions associated with a targeted disease or condition as set forth herein or in an amount sufficient to image a tumor.

The appropriate dose will vary depending on the characteristics of the subject, for example, whether the subject is a human or non-human, the age, weight, and other health considerations pertaining to the condition or status of the subject, the mode, route of administration, and number of doses, time and route of administration, other drugs or treatments being administered concurrently, as well as the specific pharmacology of the therapeutic compositions for eliciting the desired activity or biological response in the subject. Dosage regimens can be adjusted to provide an optimum prophylactic or therapeutic response.

A therapeutically effective amount is also one in which any toxic or detrimental side effects of the compound and/or other biologically active agent is outweighed in clinical terms by therapeutically beneficial effects. A non-limiting range for a therapeutically effective amount within the methods and formulations of the disclosure is about 0.0001 µg/kg body weight to about 10 mg/kg body weight per dose, such as about 0.0001 µg/kg body weight to about 0.001 µg/kg body weight per dose, about 0.001 µg/kg body weight to about 0.01 µg/kg body weight per dose, about 0.01 µg/kg body weight to about 0.1 µg/kg body weight per dose, about 0.1 µg/kg body weight to about 10 µg/kg body weight per dose, about 1 µg/kg body weight to about 100 µg/kg body weight per dose, about 100 µg/kg body weight to about 500 µg/kg body weight per dose, about 500 µg/kg body weight per dose to about 1000 µg/kg body weight per dose, or about 1.0 mg/kg body weight per dose to about 10 mg/kg body weight per dose.

D. Kits

The disclosure also provides kits that include one or more CNA molecules of this disclosure in one or more containers. In some examples, CNA molecules are lyophilized, and reconstituted before administration to a subject or any other use. Kits can optionally include other agents, such as pharmaceutically acceptable carriers, instructions, and the like.

Aspects of the forgoing are illustrated by the following non-limiting examples.

EXAMPLES

Example 1

CNA design: The CNA monomer design is inspired by the success in the utilization of peptide nucleic acids (PNAs) as a DNA mimic. The first PNA was synthesized using an aminoethylglycine (AEG) backbone, which was selected based on rudimentary molecular modeling that indicated similar repeat-unit distances and optimized bond angles to that of the phosphate-ribose backbone of DNA. Since its discovery, several variations of PNAs have been synthesized and evaluated, revealing basic structural constraints required for hybridization. The most critical constraint is the distance between pendant nucleobases along the backbone of the chain; the optimum of which is six atoms. While hybridization with ssDNA has been observed for PNAs possessing a 5- or 7-atom spacer between nucleobases, PNA backbone variations having a 6-atom spacer exhibit greater stability as indicated by their higher melting temperatures.

The structure for the initial CNA monomer has a 6-atom spacer between repeat units and contains three components: thiol, vinyl, and nucleobase (see FIG. 1). Two different monomers are initially proposed that contain these essential components while also having a 6-atom spacer between repeat units. Simulations (SYMBYL-x1.2) indicate that the repeat-unit length for the N-vinyl thiol ethylamine (VTE, see FIG. 4) is 0.34 Å less than the DNA repeat-unit length (for comparison, the difference between DNA and PNA is 0.33 Å).

Figure 7:
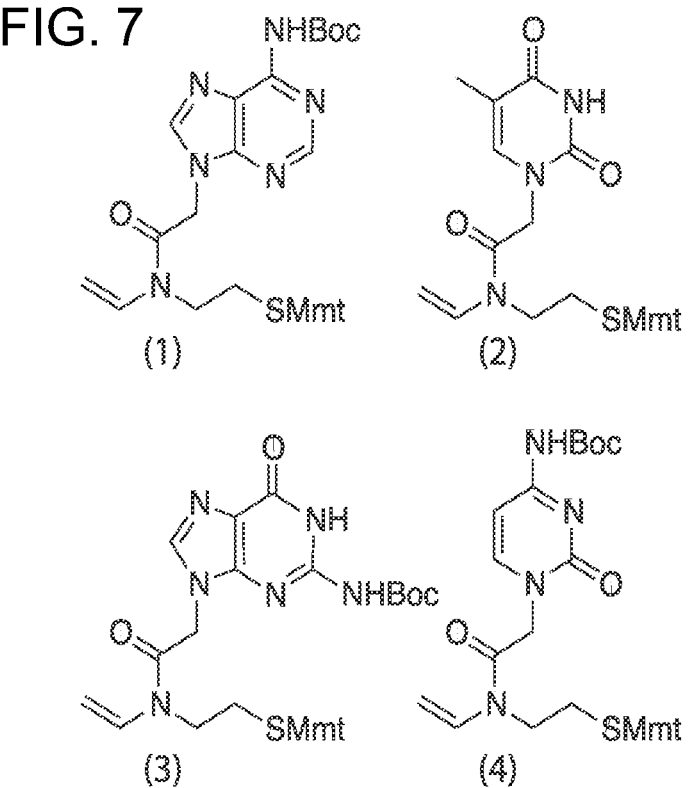
FIG. 7 shows the pendant bromoacetamide is readily coupled to any of the four nucleobases to form 1) adenine (A)-, 2) thymine (T)-, 3) guanine (G)-, and 4) cytosine (C)-CNA monomers (Boc protected).

Synthesis: The CNA monomer is synthesized from several simple molecular constituents, allowing precise, atomic level monomer design. Having this synthetic control over the monomer structure further enables simple structural variations as a possible contingency of poor solubility or hybridization efficiency or as further optimization of hybridization stability. The VTE monomer was successfully synthesized using three coupling reactions: thiol protection using a methoxytrityl group (Mmt), amide coupling, and vinyl iodide reaction with amide. The last step of coupling the cytosine to the bromoacetic acid is readily extended to the remaining three nucleobases (adenine, thymine, and guanine) to make all CNA analogs of DNA. As presented in the C-CNA was synthesized in hundreds of milligram quantities demonstrating a synthetic scheme that is readily extended to the other nucleobases: A, T, and G (FIG. 7). The remaining A-, T-, and G-CNA monomers are synthesize. The synthesis is refined to optimize yields and scale up the product to gram or larger quantities as is critical for the grand vision of utilizing these materials in applications such as SNP detection, as well antisense gene therapeutics or nanoscopic drug delivery systems.

Mmt groups provide fast and efficient deprotection of the thiol functional group; as a possible contingency plan, other orthogonally removed thiol protecting groups will be considered, such as the acetamidomethyl and nitrobenzyl functional groups. As shown in FIG. 5, the protected thiol functionality is added to the central molecule via amide coupling using 1-ethyl-3-(3-dimethylaminopropyl) carbodiimide (EDC), which is demonstrated herein to be efficient and resulted in a product that is simple to purify. The general protected-thiol-ene monomer is produced via the catalytic coupling of vinyl iodide following a procedure developed by Jiang et al. (Jiang et al. "Copper-catalyzed coupling of amides and carbamates with vinyl halides." Organic Letters 5, 3667-3669 (2003), which is incorporated herein by reference in its entirety) This base monomer is then modified by any of the four nucleobases as shown in FIG. 7.

Modifications to the CNA backbone are also considered. Exploration of different monomer structures provides insight into the molecular parameters affecting fundamental properties such as CNA solubility, thiol-ene coupling, and CNA hybridization. Preliminary molecular simulations (SYMBYL-x1.2) reveal that a N-vinyl thiol acetamide (VTA) backbone has a difference of 0.22 Å from the DNA repeat unit length (as noted earlier, the difference between PNA and DNA is 0.33 Å). Thus, as an alternate candidate we propose synthesizing the VTA-based CNA using the same coupling reactions used to make the VTE-based monomer.

Polymerization and Hybridization: The thiol of monomeric C-CNA was deprotected (FIG. 5) and fabricated a CNA oligomer via photopolymerization in the presence of oligomeric guanine-DNA (10-mer G-DNA). The product was purified by ethanol precipitation and confirmed using MALDI-TOF mass spectroscopy. Through this experiment we have established two principle findings: i) the CNA monomers are capable of being photoinitiated in the presence of DNA and ii) the thiol-ene reaction proceeds via an alternating propagation chain-transfer mechanism (see FIG. 2). These findings support the presupposition that these particular thiol and 'ene' functional groups are well suited for thiol-ene chemistry and are chemically orthogonal to the functional groups present in nucleic acid-based materials. The thiol-ene radical nature and its low concentration throughout the reaction are expected to minimize any base damage; however, as a contingency, numerous other thiol-X coupling reactions (e.g., Michael addition) could be used.

In some examples, the sequential fabrication of a CNA molecule is performed on a solid substrate (i.e., functionalized resin) to provide sequential control and aid in purification, in analogy with solid phase peptide synthesis (SPPS). Briefly, an amine functionalized cleavable substrate (often used in SPPS, e.g., Rink amide resin) is converted to thiol via standard amide coupling of a thiol-protected mercaptopropionate. The substrate enables efficient and simple reaction and purification cycles. For a given cycle, the thiol is deprotected and the byproducts rinsed away, followed by CNA monomer thiol-ene coupling to create a new thiol-protected surface (see FIG. 9). This procedure is then repeated until the desired CNA sequence is completed. Finally, the CNA oligomer is cleaved from the surface and purified by column chromatography (HPLC). The product will then be verified and further evaluated using mass spectroscopy (MALDI TOF MS).

Monomer Coupling Optimization: Coupling efficiency is evaluated for each thiol-ene reaction step; this is achieved by removing aliquots of resin throughout the CNA fabrication process and analyzing the product via HPLC and mass spectroscopy (as well as infrared and NMR spectroscopy, when appropriate). Reaction parameters are varied such as the concentrations of photoinitiator, resin, and CNA monomer; stoichiometry; irradiation intensity; and reaction time to further optimize the thiol-ene coupling efficiency. Since non-quantitative conversions result in sequential error propagation, optimization of the reaction parameters is critical. To further minimize this effect, additional reaction strategies that are commonly employed in SPPS will be considered, such as using an intermediate capping reaction to reduce error propagation (e.g., rinsing with an intermediate methyl acrylate/phosphine solution).

Figure 6:
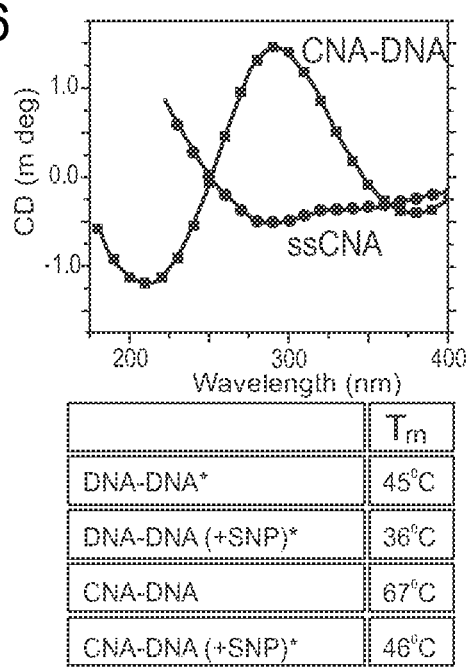
FIG. 6 shows the CD spectrograph of a C-CNA oligomer with and without complementary G-DNA (blue squares and green circles, respectively) at 25° C. (top) and melting temperatures determined via a temperature sweep (bottom). The melting temperature ($T_m$) is larger for CNA-DNA hybrids than for DNA-DNA hybrids and is more affected by single base mismatches (i.e., single nucleotide polymorphism or SNP), indicating a higher degree of stability and selectivity, respectively. *Note: DNA-DNA melting temperatures were calculated using BioMath Calculators.

Circular Dichroism: Circular dichroism (CD) spectroscopy was used to evaluate the CNA optical activity. CD spectroscopy of oligomeric C-CNA and G-DNA exhibits optical activity that is characteristic of helical secondary structure (see FIG. 6). This extraordinary result is the first example of synthetic DNA hybridization since the discovery of PNA nearly two decades ago. Moreover, a temperature sweep of the sample to 90° C. (at 2° C./min) reveals a disassociation or 'melting' temperature that is 20° C. in excess of DNA-DNA binding equivalents (FIG. 6); that is, the complementary CNA-DNA binding is more stable than DNA-DNA. Finally, the hybridization experiment was repeated except with a DNA strand that contained a single change in the sequence (i.e., a SNP). The effect of a single base mismatch was a dramatic destabilization of the DNA-CNA association, indicating that CNA materials would be exceptionally sensitive to DNA SNPs.

The capabilities of DNA to store information and selectively associate via its nucleic acid sequence and hybridization, respectively, makes DNA one of the most capable and powerful biomolecular structures. In the proposed work, we aim to create CNA oligomers that better mimic the capabilities of DNA while taking advantage of the efficient and facile nature of thiol-ene click chemistry.

Hybridization Evaluation: The hybridization of CNA with DNA is evaluated using a purchased DNA oligonucleotide (Integrated DNA Technologies, Inc.) and a fabricated CNA complement. Specifically, the melting temperature is evaluated of a 21-nucleobased DNA oligonucleotide (KRAS codon 12: 5'-CAG CTC CAA CTA CCA CAA GTT TAT-3' (SEQ ID NO: 1) and a synthesized CNA complement. Additionally considered are single and double point-mutation at the 5' and 3' ends as well as at the mid-point. Such information will be critical in assessing the effectiveness of CNA for SNP detection. As mentioned above CD spectroscopy is well suited to measure the hybridization stability (or 'melting' temperature) of the CNA-DNA complex by measuring the absorbance at 260 nm. In a typical experiment, single stranded CNA and DNA is incubated at 70° C. for 10 minutes and slowly cooled to room temperature. Protocol modifications, such as thermal cycling, will be considered for the optimization of CNA-DNA hybridization as well as to explore novel association characteristics.

Example 2

Demonstrate CNA Oligomer Detection of DNA SNPs

DNA oligonucleotide arrays consist of spots of different DNA sequences that are fixed to a solid substrate, allowing the evaluation of complementary hybridization events with a sample of genetic material. This technique is utilized in a myriad of genetic screening applications, such as genome sequencing, pathogenomics, and gene expression analysis. CNAs will enable a facile method to fabricating diagnostic DNA arrays for SNP detection. In addition to providing a route to synthesize large nucleobase polymers, thiol-ene chemistry is readily photo-induced, yielding the precise spatiotemporal control over the reaction. The fabrication of CNA arrays on a chip is achieved by directing the sequence specific growth using lasers or masked light. As a proof of concept, fluorescently labeled DNA will be purchased, and the ability of the CNA microarray to capture specific sequences is evaluated. In a specific example, the efficiency of the CNA microarray is evaluated to detect a SNP in the KRAS oncogene (C->G at codon 12), a genetic biomarker commonly associated with cancer diagnosis.

Figure 16:
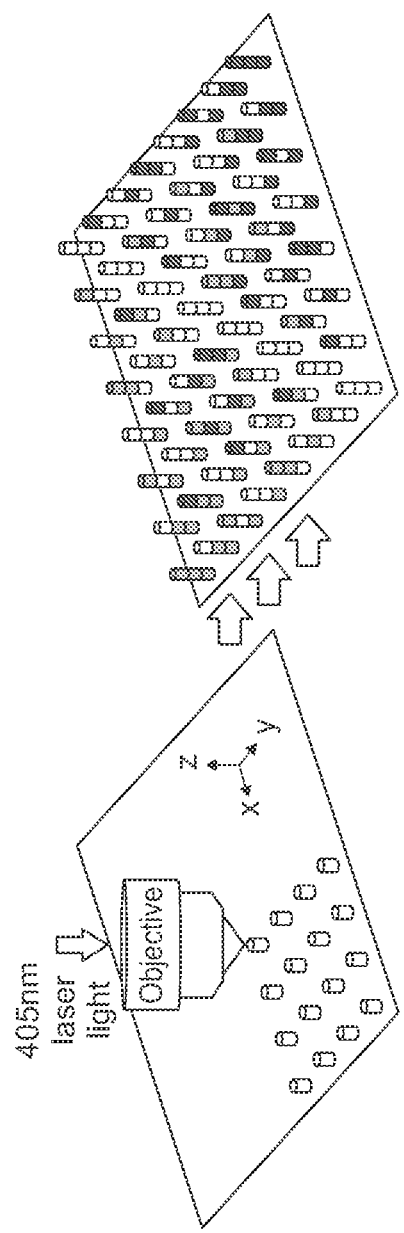
FIG. 16 is an illustration of the fabrication of an addressable, CNA array via optical direct write lithography. Initially, CNAs are spatioselectively reacted to a thiolated surface using focused laser light. Using subsequent capping to prevent error propagation, these sequences are rapidly fabricated using add, couple, rinse, and deprotect monomer synthesis cycles.
Figure 17:
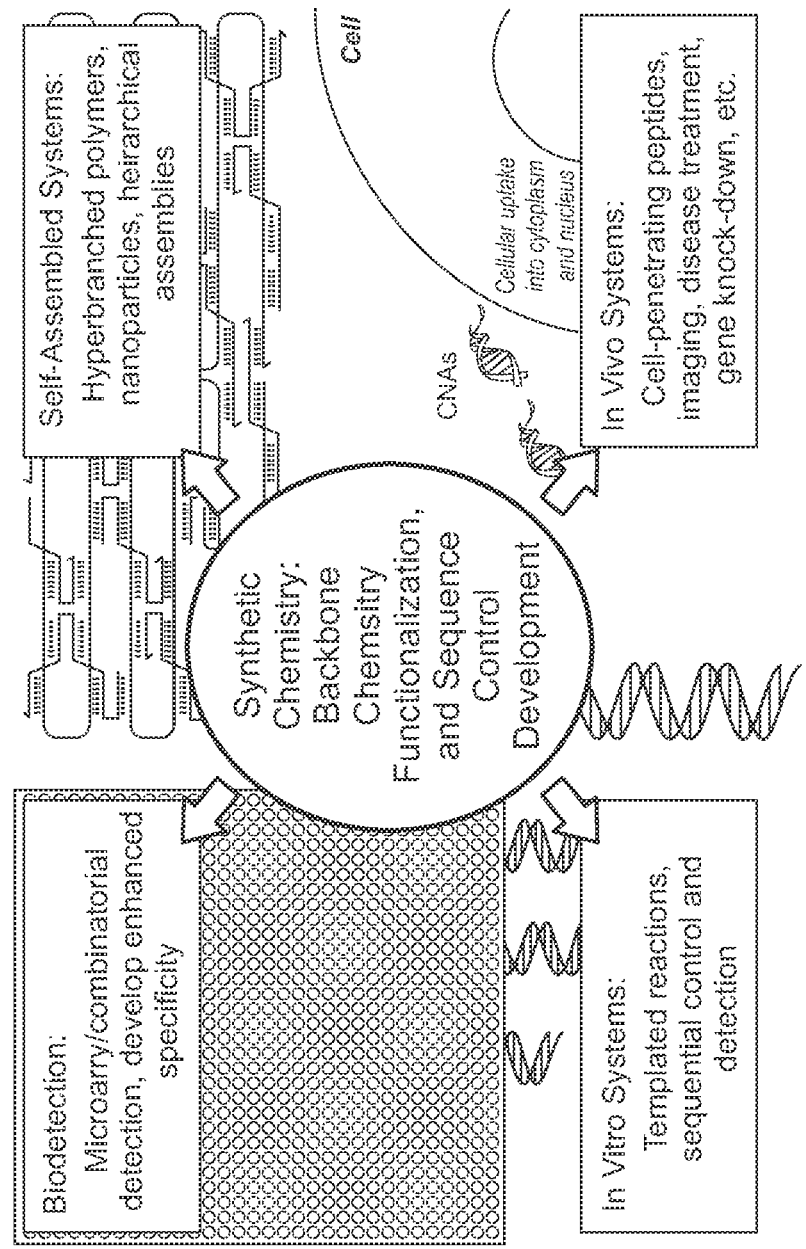
FIG. 17 is an illustration of a possible overall approach to the synthesis, development and implementation of CNAs in biology, chemistry, engineering, and materials science. CNAs, assembled by thiol-ene click chemistry, have the potential for bringing the benefits of DNA and its unique capabilities to large scale development in self-assembly, nanotechnology, medicine, and biotechnology.

Fabrication of CNA Oligonucleotide Array: Sequences of CNA oligonucleotides are directly fabricated on a thiolated glass slide. The slide is prepared by oxidation of the slide surface via a piranha solution followed by vapor deposition of a thiol-silane agent (i.e., 3-mercaptopropyltrimethoxysilane). The slide is placed on the stage of a confocal microscope equipped with a 405 nm laser. A CNA monomer solution, which can include a photoinitiator (I819—a visible light photoinitiator), is floated over the surface of the slide. The microscope is programmed to irradiate small areas on the slide using a 405 nm laser, which will establish the placement of the first CNA base (See FIG. 16). The CNA solution is rinsed away, but saved for future couplings. This process is repeated for the remaining three CNA bases, completing the first segment of the CNA oligonucleotide. A blocking solution is then be applied to the slide, consisting of a hexyl acrylate/dimethylphenylphosphine solution, which will irreversibly bind to all unreacted thiols and mitigate sequence error propagation. The thiol protecting group is then be removed and the next CNA addition/rinse cycle will begin. Using this protocol, a CNA oligomer of size N will require a maximum of 4N CNA addition/rinse cycles, where each CNA nucleotide solution is reusable. It should be appreciated that this procedure is readily expanded to create high-density oligo microarrays, and has implications well beyond the simple fabrication of a diagnostic gene array for SNP detection.

In some examples, a 20 spot CNA oligonucleotide array is created having four distinct sequences (i.e., five repeats per sequence). Two of the distinct sequences can be a 21-nucleotide complementary CNA sequence of either the wildtype or mutant KRAS codon 12 (i.e., the target sequence will be 5'-XAG CTC CAA CTA CCA CAA GTT TAT-3' (SEQ ID NO: 2), where X='C' and X='G' for wildtype and G→R mutant, respectively). The remaining two distinct sequences are the wildtype sequence with two point mutations and a nonspecific (random) control. DNA oligomers having the wildtype and mutant sequences with different fluorescently labeled end-groups (Cy3 and Cy5) are be purchased. The fluorescently labeled DNA is visualized using an Agilent Technologies Fluorescent Microarray Scanner. In each trial, the average fluorescence for a given spot will be reported relative to background and normalized to the spot containing complementary sequence. Thus, for the trial containing both wildtype and mutant DNA target sequences, each color-channel (corresponding to the Cy3 and Cy5 fluorophore) is used to determine positive binding. Furthermore, the hybridization protocol is optimized to find suitable conditions for detection of the mutant KRAS oncogene.

Example 3

Modification of Surfaces with Thioether Nucleic Acids

Figure 19:
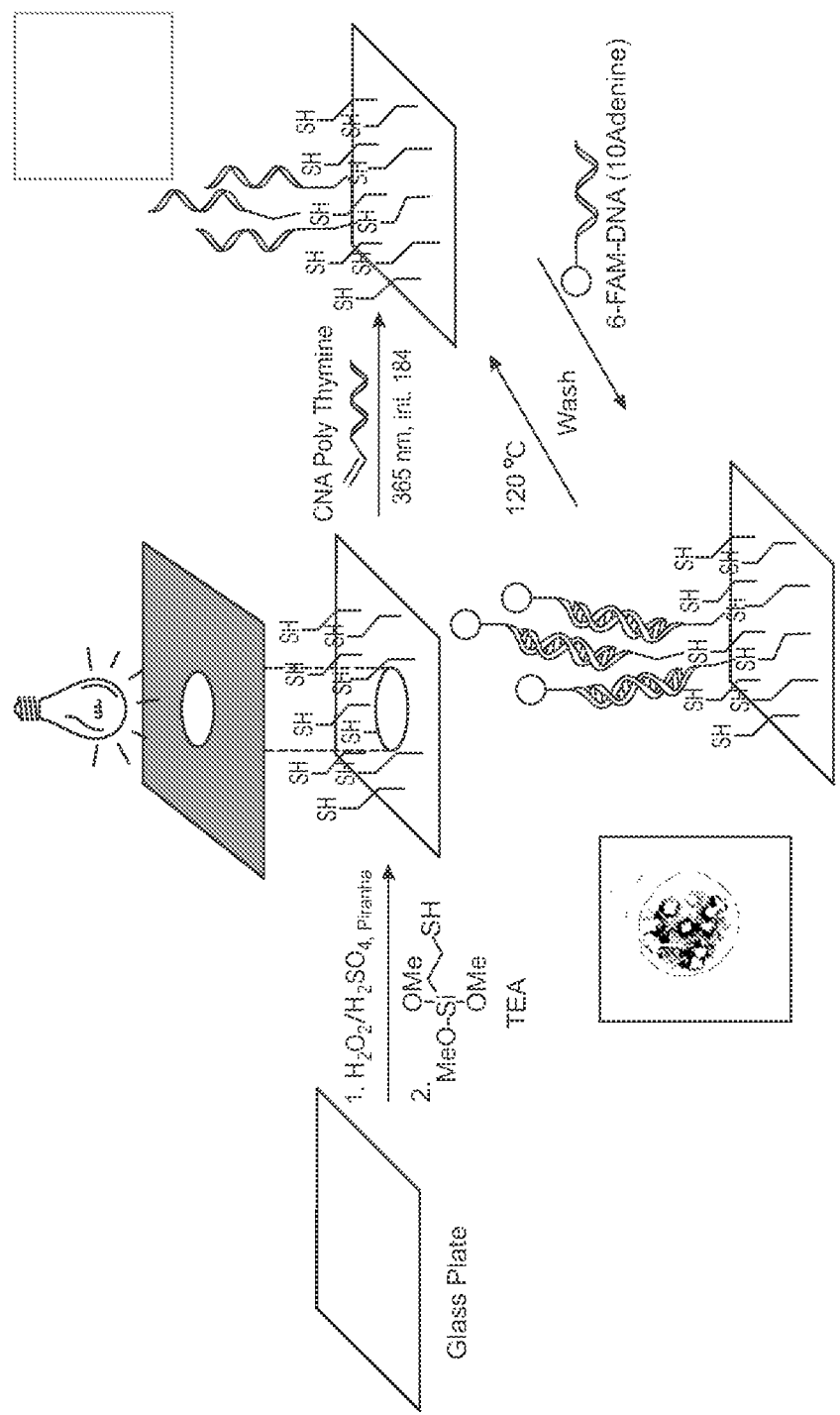
FIG. 19. is a schematic illustrating a method of modifying as surface using CNA-DNA (fluorescent) hybrid molecules.
Figure 20:
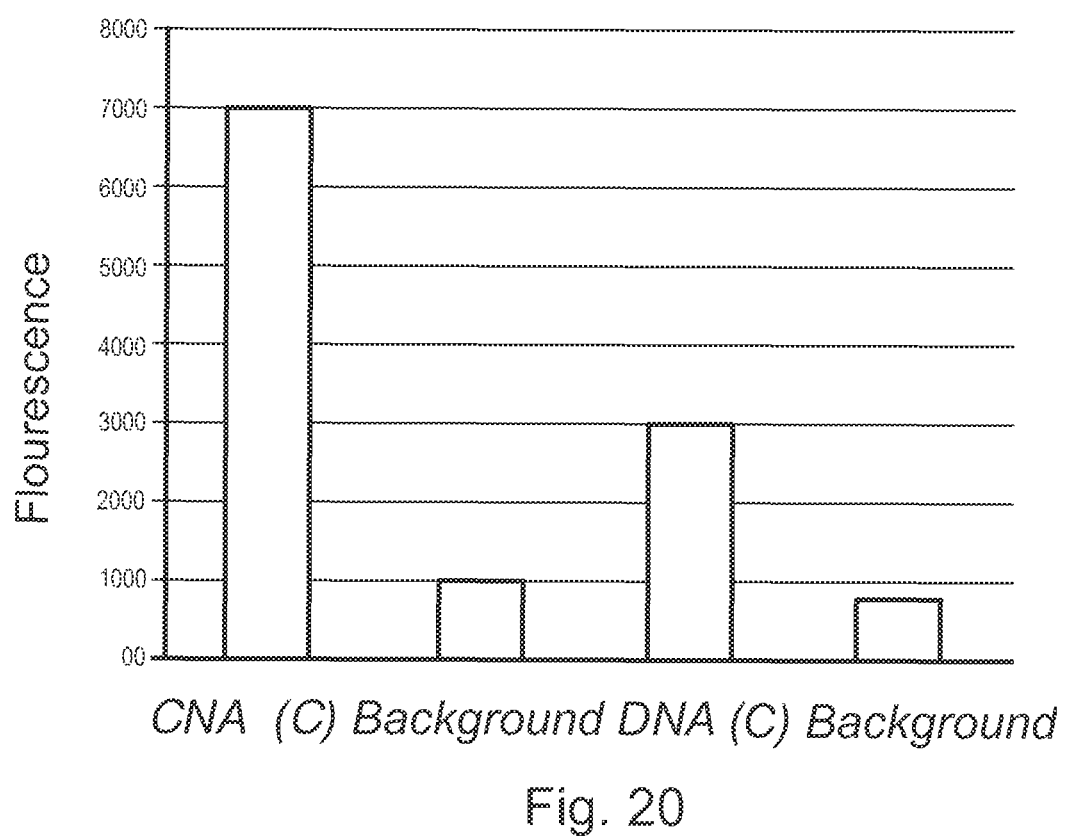
FIG. 20 is a bar graph showing the results of using fluorescence detection of CNA-DNA (F) hybrids on a surface.

A CNA sequence was incorporated into surface modification as a simple demonstration that the disclosed CNA molecules have better affinity towards complementary DNA. This increased sensitivity allows the CNA molecules sensitive probe for DNA strands detection on the surface. In this trial the first step was to attach both CNA (poly T) and DNA (poly A) strands on the glass slide with same loading (1 µM) (see FIG. 18). Excess fluorescent complementary DNA strands were used as a fluorescent probe for detection DNA and CNA on the glass slide. As shown in FIG. 19, the results of this trial indicate that our CNA has more fluorescent intensity than DNA. This data demonstrates that CNA molecules are more sensitive towards complementary DNA strands than DNA itself.

Example 4

Incorporation of Click Nucleic Acids into Hydrogels

CNA-DNA hybrids were introduced as the cross-linker in hydrogel formation. In initial trials a 4-armed PEG-poly A (DNA) and 2-armed PEG poly T(CNA) was synthesized using thiol-Michael addition with PEG-acrylate. These two substrates were mixed together in the buffer (5-8 wt %) and the formation of a hydrogel was observed. These results demonstrate the resilient nature of the disclosed CNA molecules as molecular building blocks, for example in biocompatible hydrogels.

SEQUENCE LISTING

<160> NUMBER OF SEQ ID NOS: 2

<210> SEQ ID NO 1
<211> LENGTH: 24
<212> TYPE: DNA
<213> ORGANISM: Homo sapiens

<400> SEQUENCE: 1
cagctccaac taccacaagt ttat          24

<210> SEQ ID NO 2
<211> LENGTH: 24
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is c or g

<400> SEQUENCE: 2
nagctccaac taccacaagt ttat          24

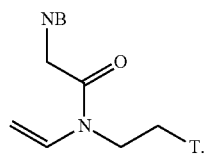
11. The click nucleic acid monomer according to claim 6, wherein the nucleobase has the formula:
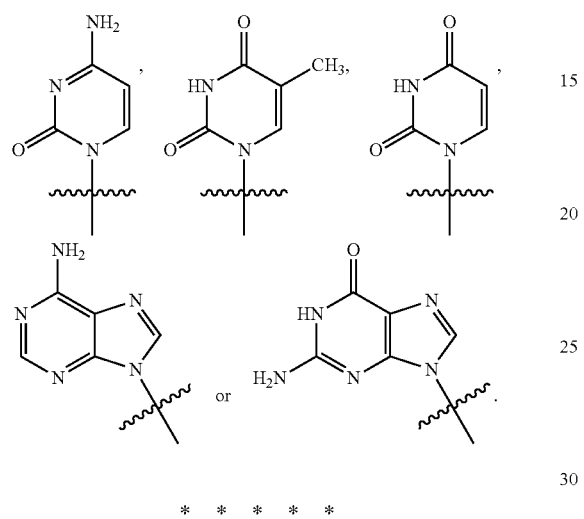

The invention claimed is:
1. A click nucleic acid monomer, having the formula:

TCA-N(NS)-T wherein T is an optionally protected thiol;
TCA is a thiol-click acceptor having the formula:

—CH=CH$_2$;

NS has the formula:

[structure: O=C-CH$_2$-NB]

NB is an optionally protected nucleobase.

2. The click nucleic acid monomer of claim 1, wherein the monomer comprises, an A, G, T, U, or C nucleobase having the formula:

[structures of C, T, U, A, G nucleobases]

3. The click nucleic acid monomer of claim 1, wherein the thiol has the formula:

[structures: —SH or —(CH$_2$)$_p$—SH]

wherein p is an integer from 0 to 4.

4. A click nucleic acid monomer having the formula:

[structure with NB, C=O, N, vinyl, and ethyl-SH]

wherein NB is a nucleobase.

5. The click nucleic acid monomer according to claim 4, wherein the nucleobase has the formula:

[structures of C, T, U, A, G nucleobases]

6. A click nucleic acid monomer having the formula:

[structure with NB, R$_5$, R$_6$, R$_7$, N, and T]

wherein:
NB is a nucleobase;
T is an optionally protected thiol;
R$_5$, R$_6$ and R$_7$ are each independently chosen from hydrogen or alkyl.

7. The click nucleic acid according to claim 6, wherein T is a thiol having the formula:

[structure: —SH]

8. The click nucleic acid according to claim 6, wherein T is a protected thiol having the formula:

[structure: —SPG]

9. The click nucleic acid according to claim 8, wherein protecting group is chosen from methoxytrityl, acetamidomethyl or nitrobenzyl.

10. The click nucleic acid according to claim 6, having the formula: